US006172104B1

(12) United States Patent
Tidwell et al.

(10) Patent No.: US 6,172,104 B1
(45) Date of Patent: Jan. 9, 2001

(54) DICATIONIC DIBENZOFURAN AND DIBENZOTHIOPHENE COMPOUNDS AND METHODS OF USE THEREOF

(75) Inventors: Richard R. Tidwell, Pittsboro; James Edwin Hall, Chapel Hill, both of NC (US)

(73) Assignee: The University of North Carolina at Chapel Hill, Chapel Hill, NC (US)

( * ) Notice: Under 35 U.S.C. 154(b), the term of this patent shall be extended for 0 days.

(21) Appl. No.: 09/344,143

(22) Filed: Jun. 24, 1999

Related U.S. Application Data

(60) Provisional application No. 60/097,273, filed on Aug. 20, 1998.

(51) Int. Cl.$^7$ .......................... A61K 31/38; A61K 31/34; C07D 333/74; C07D 307/91
(52) U.S. Cl. .......................... 514/443; 514/468; 549/48; 549/460; 549/461
(58) Field of Search ............................ 549/48, 460, 461; 514/443, 468

(56) References Cited

U.S. PATENT DOCUMENTS

| | | | | |
|---|---|---|---|---|
| 2,500,734 | * | 3/1950 | Abbott, Jr. .......................... | 549/460 |
| 3,201,418 | * | 8/1965 | McCall et al. ...................... | 549/48 |
| 3,218,337 | * | 11/1965 | McCall et al. ...................... | 549/48 |
| 4,362,883 | * | 12/1982 | Harvey ................................ | 549/460 |

FOREIGN PATENT DOCUMENTS

| | | |
|---|---|---|
| 0 366 066 | 5/1990 | (EP) . |
| 96 15126 | 5/1996 | (WO) . |
| 96 40114 | 12/1996 | (WO) . |
| 96/40117 | 12/1996 | (WO) . |
| 97 17949 | 5/1997 | (WO) . |

OTHER PUBLICATIONS

Fujikawa et al, "Method for producing 4–methyl and 4,6–dimetyl dibenzothiophene", CA124:145884, 1996.

Nair et al, "Preparation of substituted dibenzothiophenes as immunomodulators and antitumor agents", CA112:235168, 1990.

Shiseido Co., "Perfumes containing dibenzothiophenes", CA102:84267, 1985.

Boykin et al.; "Dicationic Diarylfurans as Anti–Pneumocystic carinii Agents," *Journal of Medicinal Chemistry* 38, No. 6, pp. 912–916 (1995).

Steinhein De; *Catalogue Handbook of Fine Chemicals, Aldrich–Chemie GMBH*, XP–002120369, p. 403 (1990).

Tidwell et al., "Activity of Cationically Substituted Bis––Benzimidazoles against Experimental Pneumocystic carinii Pneumonia," *Antimicrobial Agents and Chemotherapy*, 37, No. 8, pp. 1713–1716 (1993).

Wang Sihe et al.; "Dicationic dibenzofurans as anti–pneumocystis carinii pneumonia agents," *Book of Abstracts, 215$^{th}$ ACS National Meeting, Dallas*, MEDI–031 , XP–002120370 Abstract, (1998).

Wilson et al.; "The Search for Structure–Specific Nucleic Acid–Interactive Drugs: Effects of Compound Structure on RNA versus DNA Interaction Strength," *Biochemistry*, 32, pp. 4098–4104 (1993).

International Search Report for PCT/US/99/14313, dated Nov. 11, 1999.

J.S. Moffatt; 135. 3 : 6–Diamidinodibenzofuran., *Notes.*, pp. 625–626 (1951).

* cited by examiner

*Primary Examiner*—Deborah C. Lambkin
(74) *Attorney, Agent, or Firm*—Myers Bigel Sibley & Sajovec

(57) ABSTRACT

Methods of treating *Pneumocystis carinii* pneumonia comprise administering a therapeutically effective amount of a dicationic dibenzofuran compound described by Formula (I). Methods of treating *Pneumocystis carinii* pneumonia also comprise administering a therapeutically effective amount of a dicationic dibenzothiophene compound described by Formula (II). Novel compounds are also disclosed, and are represented by the Formulae (I) and (II).

33 Claims, No Drawings

US 6,172,104 B1

DICATIONIC DIBENZOFURAN AND DIBENZOTHIOPHENE COMPOUNDS AND METHODS OF USE THEREOF

This application claims the benefit of U.S. Provisional application Ser. No. 60/097,273, filed Aug. 20, 1998, the disclosure of which is incorporated by reference herein in its entirety.

The present invention was made with Government support under Grant Number HI-33363 from the National Institutes of Health. The Government has certain rights to this invention.

FIELD OF THE INVENTION

The present invention concerns dicationic dibenzofurans and dicationic dibenzothiophenes, and the use thereof in the treatment of *Pneumocystis carinii* pneumonia.

BACKGROUND OF THE INVENTION

A number of aromatic diamidines have been shown to bind to the minor-groove of DNA, and to exhibit useful antimicrobial activity. Various hypotheses of the mode of antimicrobial action of the aryl amidines have been proposed. However, evidence is growing that these compounds function by complex formation with DNA and subsequent selective inhibition of DNA dependent microbial enzymes. Intervention in transcription control has been demonstrated and seems to be a plausible mode of action for structurally diverse minor groove binders. (Das, B. P.; Boykin, D. W., *J. Med. Chem.* 1977, 20, 531–536; Boykin, D. W. et al.,*J. Med. Chem.* 1995, 36, 912–916; Kumar, A. et al., *Eur. J. Med. Chem.* 1996, 31, 767–773; Lombardy, R. J. et al., *J. Med. Chem.* 1996, 31, 912–916; Tidwell, R. R. et al.,*Antimicrob. Agents Chemother.* 1993, 37, 1713–1716; Tidwell, R. R.; Bell, C. A., Pentamidine and Related Compounds in Treatment of *Pneumocystis carinii* Infection, in *Pneumocystis carinii*, Ed Marcel Decker; New York, 1993, 561–583; Henderson, D.; Hurley, L. H., *Nature Med.* 1995, 1, 525–527; Mote, J. Jr., et al., *J. Mol. Biol.* 1994, 226, 725–737; Boykin, D. W., et al., *J. Med. Chem.* 1998, 41, 124–129).

PCT Application No. WO96/40117 (Dec. 19, 1996) describes dicationic substituted carbazoles and the use thereof in treating *Pneumocystis carinii* pneumonia (PCP), *Cryptococcus neoformans, Cryptosporidium parvum,* and *Candida albicans.*

J. Moffatt, *J. Chem. Soc.* 1951, 625–626, describes 3:6-diamidinodibenzofuran, and the use thereof in the treatment of as a trypanocide.

SUMMARY OF THE INVENTION

A first aspect of the present invention is a compound having the formula:

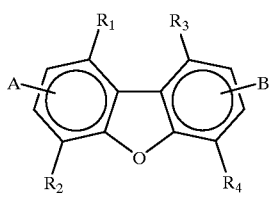

(I)

wherein:

$R_1$, $R_2$, $R_3$, and $R_4$ are each independently selected from the group consisting of H, loweralkyl, oxyalkyl, aryl, alkylaryl, aminoalkyl, aminoaryl, oxyaryl, oxyarylalkyl, or halogen;

A and B are each selected from the group consisting of H, loweralkyl, oxyalkyl, and

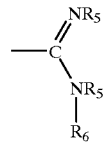

wherein:

each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl;

or a pharmaceutically acceptable salt thereof; subject to the proviso that said compound is not 3:6-diamidinodibenzofuran.

A second aspect of the present invention is a method of treating *Pneumocystis carinii* pneumonia in a subject in need of such treatment, comprising administering to said subject a compound having the formula:

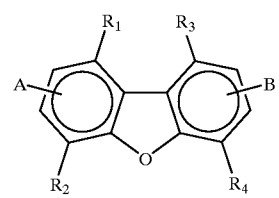

(I)

wherein:

$R_1$, $R_2$, $R_3$, and $R_4$ are each independently selected from the group consisting of H, loweralkyl, oxyalkyl, aryl, alkylaryl, aminoalkyl, aminoaryl, oxyaryl, oxyarylalkyl, or halogen;

A and B are each selected from the group consisting of H, loweralkyl, oxyalkyl, and

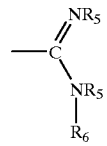

wherein:

each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl;

or a pharmaceutically acceptable salt thereof.

A third aspect of the present invention compound having the formula:

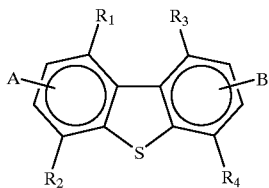

(II)

wherein:

$R_1$, $R_2$, $R_3$, and $R_4$ are each independently selected from the group consisting of H, loweralkyl, oxyalkyl, aryl, alkylaryl, aminoalkyl, aminoaryl, oxyaryl, oxyarylalkyl, or halogen;

A and B are each selected from the group consisting of H, loweralkyl, oxyalkyl, and

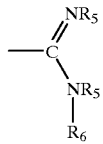

wherein:

each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl;

or a pharmaceutically acceptable salt thereof.

A fourth aspect of the present invention is a method of treating *Pneumocystis carinii* pneumonia in a subject in need of such treatment, comprising administering to said subject a compound having the formula:

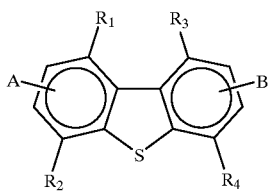

(II)

wherein:

$R_1$, $R_2$, $R_3$, and $R_4$ are each independently selected from the group consisting of H, loweralkyl, oxyalkyl, aryl, alkylaryl, aminoalkyl, aminoaryl, oxyaryl, oxyarylalkyl, or halogen;

A and B are each selected from the group consisting of H, loweralkyl, oxyalkyl, and

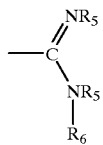

wherein:

each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl;

or a pharmaceutically acceptable salt thereof.

Compounds according to formula (I) or (II) above and the pharmaceutically acceptable salts thereof, pharmaceutical formulations containing the same, and the use of compounds of formula (I) or (II) and the pharmaceutically acceptable salts thereof for the preparation of a medicament for treating *Pneumocystis carinii* pneumonia, are also an aspect of the present invention.

The foregoing and other objects and aspects of the present invention are explained in detail in the specification set forth below.

DETAILED DESCRIPTION OF THE INVENTION

The term "loweralkyl," as used herein, refers to $C_1$–$C_6$ linear or branched alkyl, such as methyl, ethyl, propyl, isopropyl, butyl, sec-butyl, iso-butyl, tert-butyl, pentyl, isopentyl, and hexyl. Isoalkyl groups, such as isopropyl, isobutyl, isopentyl, and the like are currently preferred. The term "loweralkoxy" or "oxyalkyl" as used herein, refers to $C_1$–$C_6$ linear or branched alkoxy, such as methoxy, ethoxy, propyloxy, butyloxy, isopropyloxy, and t-butyloxy. Methoxy is currently preferred.

As noted above, the methods of the present invention are useful for treating *Pneumocystis carinii* pneumonia. The methods of the present invention are useful for treating these conditions in that they inhibit the onset, growth, or spread of the condition, cause regression of the condition, cure the condition, or otherwise improve the general well being of a subject inflicted with, or at risk of contracting the condition.

In one embodiment of the foregoing, A and B are each:

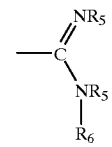

wherein:

$R_1$ is H, $R_2$ is H or loweralkyl, $R_3$ is H, $R_4$ is H, $R_5$ is H, and $R_6$ is isoalkyl; and the pharmaceutically acceptable salts thereof.

In another embodiment of the foregoing, A and B are each:

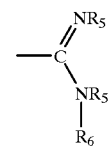

wherein:

$R_1$ is H, $R_2$ is H, $R_3$ is H, $R_4$ is H, $R_5$ is H, and $R_6$ is $C_3$–$C_8$ alkoxyalkyl; and the pharmaceutically acceptable salts thereof.

In another embodiment of the foregoing, A and B are each:

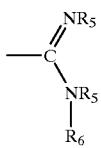

wherein:
R₁ is H, R₂ is H or loweralkyl, R₃ is H, R₄ is H, R₅ is H, and R₆ is alkylhydroxy; and the pharmaceutically acceptable salts thereof.

In another embodiment of the foregoing, A and B are each:

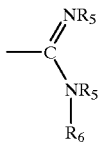

wherein:
R₁ is H, R₂ is H or loweralkyl, R₃ is H, R₄ is H, R₅ is H, and R₆ is propoxyethyl; and the pharmaceutically acceptable salts thereof.

In another embodiment of the foregoing, A and B are each:

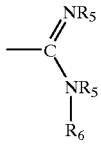

wherein:
R₁ is H, R₂ is H or loweralkyl, R₃ is H, R₄ is H, R₅ is H, and R₆ is propoxyisopropyl; and the pharmaceutically acceptable salts thereof.

In another embodiment, A and B are each:

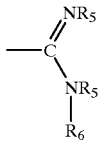

wherein:
R₁ is H, R₂ is H or loweralkyl, R₃ is H, R₄ is H, R₅ is H, and R₆ is aryl or alkylaryl; and the pharmaceutically acceptable salts thereof.

In another embodiment, A and B are each:

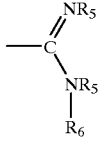

wherein:
R₁ is H, R₂ is H or loweralkyl, R₃ is H, R₄ is H, R₅ is H, and R₆ is alkylcycloalkyl; and the pharmaceutically acceptable salts thereof.

Subjects to be treated by the methods of the present invention are typically human subjects although the methods of the present invention may be useful with any suitable subject known to those skilled in the art. As noted above, the present invention provides pharmaceutical formulations comprising the aforementioned compounds of Formula (I) and (II), or pharmaceutically acceptable salts thereof, in pharmaceutically acceptable carriers for aerosol, oral, and parenteral administration as discussed in greater detail below. Also, the present invention provides such compounds or salts thereof which have been lyophilized and which may be reconstituted to form pharmaceutically acceptable formulations for administration, as by intravenous or intramuscular injection.

The therapeutically effective dosage of any specific compound, the use of which is in the scope of present invention, will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration. The duration of the treatment is usually once per day for a period of two to three weeks or until the condition is essentially controlled. Lower doses given less frequently can be used to prevent or reduce the incidence or recurrence of the infection.

In accordance with the present method, a compound of Formula (I) and (II), or a pharmaceutically acceptable salt thereof, may be administered orally or through inhalation as a solid, or may be administered intramuscularly or intravenously as a solution, suspension, or emulsion. Alternatively, the compound or salt may also be administered by inhalation, intravenously or intramuscularly as a liposomal suspension. When administered through inhalation the compound or salt should be in the form of a plurality of solid particles or droplets having a particle size from about 0.5 to about 5 microns, preferably from about 1 to about 2 microns.

Besides providing a method for treating *Pneumocystis carinii* pneumonia, the compounds of Formula (I) and (II) also provide a method for prophylaxis against *Pneumocystis carinii* pneumonia in an immunocompromised patient, such as one suffering from AIDS, who has had at least one episode of *Pneumocystis carinii* pneumonia, but who at the time of treatment is not exhibiting signs of pneumonia. As *Pneumocystis carinii* pneumonia is an especially potentially devastating disease for immunocompromised patients it is preferable to avoid the onset of *Pneumocystis carinii* pneumonia, as compared to treating the disease after it has become symptomatic. Accordingly, the present invention provides a method for the prophylaxis against *Pneumocystis carinii* pneumonia comprising administering to the patient a prophylactically effective amount of a compound of Formula (I) or (II) or a pharmaceutically acceptable salt thereof. The forms for administration of the compound or salt in accordance with this method may be the same as utilized for the purpose of actually treating a patient suffering from *Pneumocystis carinii* pneumonia.

An additional useful aspect of the present invention is a method for prophylaxis against even an initial episode of *Pneumocystis carinii* pneumonia in an immunocompromised patient who has never experienced an episode of *Pneumocystis carinii* pneumonia. In this respect, a patient who has been diagnosed as being immunocompromised, such as one suffering from AIDS or ARC (AIDS related complex), even before the onset of an initial episode of *Pneumocystis carinii* pneumonia, may avoid or delay suffering from the infection by having administered a prophylactically effective amount of a compound of Formula (I) or (II) or a pharmaceutically acceptable salt thereof. The compound or salt may be administered in the same fashion as in the treatment of patients suffering from *Pneumocystis carinii* pneumonia.

The present invention also provides new pharmaceutical compositions suitable for intravenous or intramuscular injection. The pharmaceutical compositions comprise a compound of Formula (I) or (II), or a pharmaceutically acceptable salt thereof, in any pharmaceutically acceptable carrier. If a solution is desired, water is the carrier of choice with respect to water-soluble compounds or salts. With respect to the water-insoluble compounds or salts, an organic vehicle, such as glycerol, propylene glycol, polyethylene glycol, or mixtures thereof, may be suitable. In the latter instance, the organic vehicle may contain a substantial amount of water. The solution in either instance may then be sterilized in any suitable manner, preferably by filtration through a 0.22 micron filter. Subsequent to sterilization, the solution may be filled into appropriate receptacles, such as depyrogenated glass vials. Of course, the filling should be done by an aseptic method. Sterilized closures may then be placed on the vials and, if desired, the vial contents may be lyophilized.

In addition to compounds of Formula (I) or (II) or their salts, the pharmaceutical compositions may contain other additives, such as pH adjusting additives. In particular, useful pH adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In yet another aspect of the present invention, there is provided an injectable, stable, sterile composition comprising a compound of Formula (I) or (II), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into man. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Other pharmaceutical compositions may be prepared from the compounds of Formula (I) or (II), or salts thereof, such as aqueous base emulsions. In such an instance, the composition will contain a sufficient amount of pharmaceutically acceptable emulsifying agent to emulsify the desired amount of the compound of Formula (I) or (II) or salt thereof. Particularly useful emulsifying agents include phosphatidyl cholines, and lecithin.

Further, the present invention provides liposomal formulations of the compounds of Formula (I) or (II) and salts thereof. The technology for forming liposomal suspensions is well known in the art. When the compound of Formula (I) or (II) or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds of Formula (I) or (II) or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of the desired compound of Formula (I) or (II) or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the solid compound of Formula (I) or (II), or a salt thereof, in any appropriate manner known in the art, such as by micronization. Most preferably, the size of the solid particles or droplets will be from about 1 to about 2 microns. In this respect, commercial nebulizers are available to achieve this purpose.

Preferably, when the pharmaceutical formulation suitable for administration as an aerosol is in the form of a liquid, the formulation will comprise a water-soluble compound of Formula (I) or (II) or a salt thereof, in a carrier which comprises water. A surfactant may be present which lowers the surface tension of the formulation sufficiently to result in the formation of droplets within the desired size range when subjected to nebulization.

As indicated, the present invention provides both water-soluble and water-insoluble compounds and salts. As used in the present specification, the term "water-soluble" is meant to define any composition which is soluble in water in an amount of about 50 mg/ml, or greater. Also, as used in the present specification, the term "water-insoluble" is meant to define any composition which has solubility in water of less than about 20 mg/ml. For certain applications, water soluble compounds or salts may be desirable whereas for other applications water-insoluble compounds or salts likewise may be desirable.

As indicated, the compounds used in the present invention may be present as pharmaceutically acceptable salts. Such salts include the gluconate, lactate, acetate, tartarate, citrate, phosphate, borate, nitrate, sulfate, and hydrochloride salts.

The salts of the present invention may be prepared, in general, by reacting two equivalents of the base compound with the desired acid, in solution. After the reaction is complete, the salts are crystallized from solution by the addition of an appropriate amount of solvent in which the salt is insoluble.

The compounds of the present invention are useful not only in methods for treating *Pneumocystis carinii* pneumonia, but also in methods of inhibiting enzymes such as topoisomerase. The compounds of Formula (I) or (II) are particularly useful for inhibiting topoisomerase II. See, S. Doucc-Racy, et al., *Proc. Natl. Acad. Sci. USA* 83:7152 (1986).

The present invention is explained in greater detail in the following non-limiting examples. Compounds are numbered and described separately in each example.

EXAMPLE 1

Synthesis and Anti-*Pneumocystis carinii* Pneumonia Activity of Novel Dicationic Dibenzothiophenes This example investigates the anti-PCP activity of dicationic dibenzothiophenes. Several compounds showed potent anti-PCP activity when administered intravenously, and one diamidoxime exhibited oral activity.

A. Chemistry

The 2,8-bis cationic dibenzothiophenes were prepared from dibenzothiophene (Scheme 1). Dibenzothiophene was brominated following a known procedure (Campaigne, E.; Ashby, J. *J. Heterocyclic Chem.* 1969, 6, 517–522), and the 2,8-dibromo intermediate underwent cyanodebromination to give dinitrile 10. (DuVernet, R. B. et al., *J. Am. Chem. Soc.* 1978, 100, 2457–2464.) Compounds 1–4 were prepared by standard Pinner syntheses (Patrick, D. A. et al.,. *Eur. J. Med. Chem.* 1997, 32, 781–793.; Tidwell, R. R.; et al., *J. Med. Chem.* 1990, 33, 1252–1257; Pinner, A.; Klein, F. *Chem. Ber.* 1877, 10, 1889–1897; Pinner, A.; Klein, F. *Chem. Ber.* 1878, 11, 4–11; Pinner, A. *Chem. Ber.* 1883, 16, 352–363.) from 10. The Pinner synthesis was chosen for amnidoximes 3 and 4 because of previous experience with carbazole and dibenzofuran analogues, which could not be prepared by direct reaction of the nitrile precursors with hydroxylamine (Clement, B.; et al., *Drug. Res.* 1985, 35 (II), 1009–1014). The hemimaleate salt 3 was originally prepared because the dihydrochloride salt 4 was predicted to have limited water solubility. Surprisingly, treatment of the free base of 3 with an excess of maleic acid gave the monohemimaleate salt rather than the expected dihemimaleate. Dihydrochloride salt 4, however, proved to be sufficiently water soluble for the PCP assay. The imidazoline 5 was conveniently prepared by the neat fusion of dinitrile 10 with a mixture of ethylenediamine and ethylenediamine dihydrochloride at 300° C.

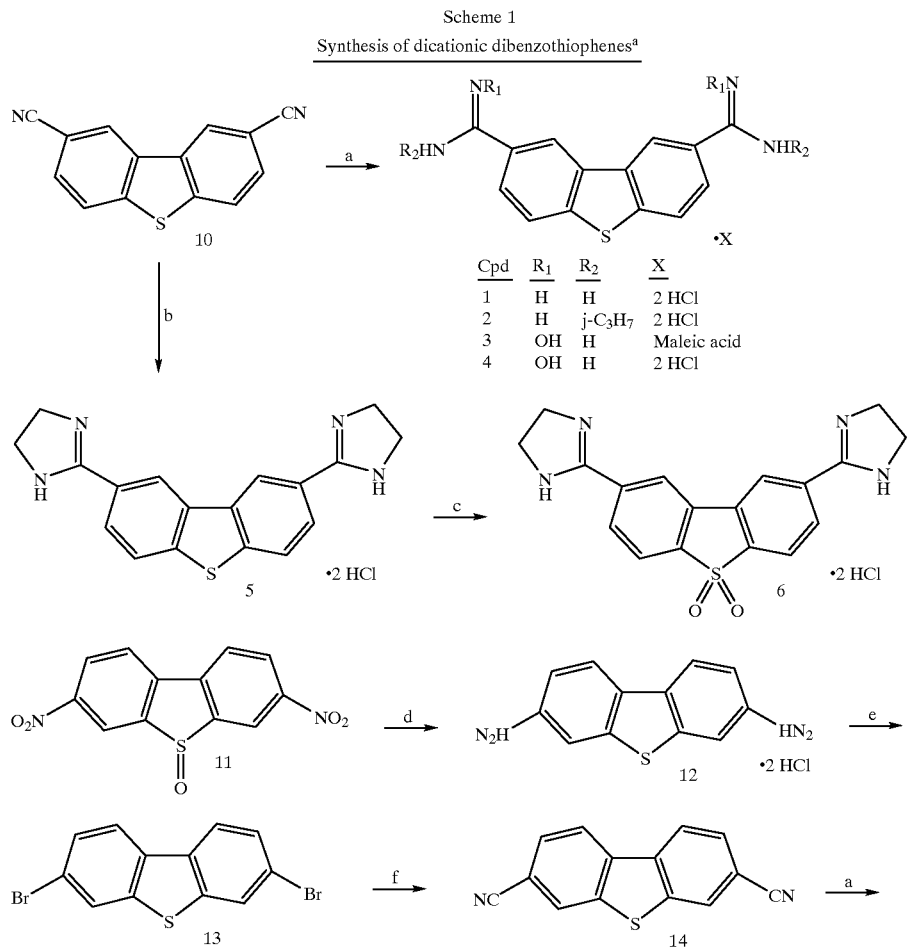

Scheme 1
Synthesis of dicationic dibenzothiophenes[a]

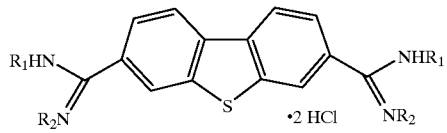

| Cpd | R₁ | R₂ |
|---|---|---|
| 7 | H | H |
| 8 | j-C₃H₇ | H |
| 9 | H | OH |

[a]Key: (a) EtOH, HCl, 1,4-dioxane-5 to 25° C., then appropriate amine, EtOH; (b) H₂N(CH₂)₂NH₂•2 HCl, H₂N(CH₂)₂NH₂, 300° C., 30 min; (c) 30% H₂O₂, TFA, 16h; (d) H₂, 10% Pd/C, EtOH, 2 h, then EtOH/HCl; (e) NaNO₂, aq. HCl, 0 C, 45 min, then CuBr, 48% HBr, Δ, 2 h; (f) CuCN, 1-methyl-2-pyrrolidinone, 3 h.

It was anticipated that sulfone analogs of the dibenzothiophene dications would be more water-soluble than the corresponding dibenzothiophenes, hence the representative sulfone 6 was prepared. The most expedient method of preparing 6 proved to be the oxidation of 5. Compound 10 (DuVernet, R. B. et al., *J. Am. Chem. Soc.* 1978, 100, 2457–2464) and its dibromo precursor (Campaigne, E.; Ashby, J. *J. Heterocyclic Chem.* 1969, 6, 517–522) were successfully oxidized to the corresponding sulfones (in 77 and 90% yields, respectively) using 30% hydrogen peroxide in acetic acid (Gilman, H.; Esman, D. L. *J. Org. Chem.* 1954, 76, 5786– 5787; Kruber, O. *Chem. Ber.* 1920, 53, 1566–1567). However, these intermediates proved to be extremely insoluble in organic solvents. An attempted Pinner synthesis beginning with the sulfone analog of 10 failed to give the desired amidine. The hydrogen peroxide oxidation of 5 in acetic acid was sluggish, presumably due to the low solubility of the starting material in acetic acid. The oxidation of 5 to 6 proceed well when trifluroacetic acid was used in place of acetic acid. The resultant ditrifluoroacetate salt was converted to the free base using sodium hydroxide, and then to the dihydrochloride salt using ethanolic HCl.

The preparation of the 3,7-dications 7–9 was less straightforward. The literature provided little insight for ring closure reactions yielding dibenzothiophenes with desired substituents in place. A different approach would involve electrophilic substitution (at positions 3 and 7) of the sulfone or sulfoxide derivative of dibenzothiophene. The dibromo intermediate 13 has been prepared by the dibromination of dibenzothiophene sulfone (Kruber, O. *Chem. Ber.* 1920, 53, 1566–1567; Cullinane, N. M. et al., *J. Chem. Soc.* 1936, 1435–1437), followed by the lithium aluminum hydride reduction of the sulfone moiety (Gerdil, R.; Lucken, E. A. C.. *J. Am. Chem. Soc.* 1965, 87,) Both of these reported procedures proved to be difficult to reproduce. The bromination step, which requires refluxing in neat bromine, resulted in a mixture of mono and dibromo products, the separation of which was hindered by their poor solubility. The hydride reduction resulted in a combination of deoxygenation and debromination products. Therefore the sulfone approach was abandoned in favor of the sulfoxide approach, as sulfoxides are known to undergo substitution and reduction under milder conditions (Brown, R. K. et al., *J. Org. Chem.* 1952, 74, 1165–1167). The attempted oxidation of dibenzothiophene by a known chlorination-hydrolysis method (Brown, R. K. et al., *J. Org. Chem.* 1948, 70, 1748–1749) resulted in 2,8-dichlorodibenzothiophene. Dibenzothiophene sulfoxide was prepared successfully by the ceric ammonium nitrate oxidization of dibenzothiophene (Ho, T. -L.; Wong, C. M.. *Synthesis* 1972, 561–562). There appeared to be no report in the literature of the direct bromination of dibenzothiophene sulfoxide. Attempted bromination resulted in no reaction using various solvents, or in mixtures of products using neat bromine. The sulfoxide was nitrated to intermediate 11 by a known procedure (Brown, R. K. et al., *J. Org. Chem.* 1952, 74, 1165–1167). The same authors reported the stannous chloride reduction of 11 to 12 (isolated as the free base). This reaction proved to be difficult to reproduce. A more expedient method was the palladium-catalyzed hydrogenation of 11 in ethanol, with the isolation of 12 as the dihydrochloride salt. The best method to prepare 14 from 12 was via intermediate 13. Dihydrochloride salt 12 readily underwent bis-diazotization with sodium nitrate in aqueous HCl, and the diazonium salt was reacted with a solution of copper(I) bromide in 48% HBr to give dibromo intermediate 13. Reaction of 13 with copper(I) cyanide in 1-methyl-2-pyrrolidinone (DuVernet, R. B. et al., *J. Am. Chem. Soc.* 1978, 100, 2457–2464) gave dinitrile 14. The dintirile was subjected to standard Pinner conditions to give the 3,7-diamidines 7–9.

B. Results and Discussion

Activity against *P. carinii* Pneumonia

The activity of the compounds against PCP in the rat model of disease is shown in Table 1. The activity is expressed as the percent of cysts counted in treated groups as compared to untreated controls. All of the compounds in the initial screen were given by tail vein injection at a dose of 10 μmol/kg/day for 14 days. The test compounds were compared for efficacy with the standard anti-PCP compound, pentamidine, at one-half the dose of pentamidine. Three of the nine compounds tested were found to be more potent than the standard drug. It was also noteworthy that none of the compounds exhibited significant toxicity in the rat model at the screening dose (10 μmol/kg). Compounds 1, 2, and 8 proved to be highly potent against the organism, producing a greater than 99% reduction in parasite load. Among the 2,8-substituted derivatives, the diamidine 1 and the bis-N-isopropylamidine 2 were very potent. A dose response study was performed upon compound 2. No toxicity was observed when the dose was lowered to 5 μmol/kg, and a greater than 99% reduction in parasite load was still observed at 2.5 μmol/kg. The diimidazoline 5 showed low activity. The sulfone analog 6 was inactive. Among the 3,7-substituted compounds, the bis-N-isopropyl amidine 8 was very active, while the diamidine 7 was only slightly active.

The diamidoximes 3 and 4 proved act as prodrugs of 1 in vivo. Both the hemimaleate salt 3 and the dihydrochloride salt 4 were approximately as active as pentamidine when given intravenously. However, 4 proved to be substantially less toxic and somewhat more potent than 3 when the prodrugs were given orally. The diamidoxime 9 proved to be inactive by both intravenous and oral administration. This result was expected due to the very low activity of the corresponding diamidine 7.

The most notable structure-activity observations arise upon comparing the anti-PCP activities of the dibenzothiophenes to those of the dibenzofuran and carbazoles (Patrick, D. A. et al.,. *Eur. J. Med. Chem.* 1997, 32, 781–793; Hall, J. E. et al., *Antimicrob. Agents Chemother.* 1998, 42, 666–674). Diamidoximes 3 and 4 proved to be orally bioavailable prodrugs of 1. In contrast, the carbazole diamidoximes were inactive or only slightly active, even thought the corresponding amidines were highly active. The activities of the dibenzothiophenes are qualitatively similar to those of the dibenzofurans, but the dibenzothiophenes are somewhat more active. Both groups showed good activity for the 2,8 and 3,7-bis-N-isopropylamidines and the 2,8-diamidines. Both groups showed reduced activity or lack of activity for the diimidazolines and the 3,7-diamidines. In contrast, the carbazole 3,6 and 2,7-diimidazolines and 2,7-diamidines were highly active. Another notable observation was the diminished activity resulting from the replacement of the dibenzothiophene sulfur atom with a sulfone group.

TABLE 1

Activity against *Pneumocystis carinii* pneumonia (PCP) by novel dicationic dibenzothiophenes.

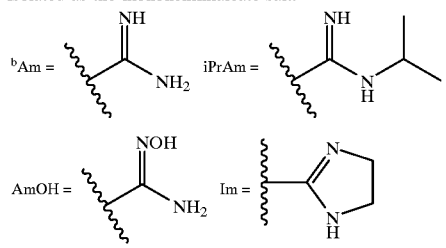

| Compound[a] | Position of R | R[b] | X | Dose[c] | Toxicity[d] | *Pneumocystis carinii* % Saline control ± std error[e] |
|---|---|---|---|---|---|---|
| Saline control | — | — | — | — | 0 | 100.00 ± 14.86 |
| Pentamidine | — | — | — | 22.0 | ++ | 0.74 ± 0.12 |
| 1 | 2, 8 | Am | S | 10.0 | 0 | 0.10 ± 0.03 |
| 2 | 2, 8 | iPrAm | S | 10.0 | + | 0.01 ± 0.01 |
|  |  |  |  | 5.0 | 0 | 0.04 ± 0.01 |
|  |  |  |  | 2.5 | 0 | 0.19 ± 0.10 |
|  |  |  |  | 1.0 | 0 | 12.76 ± 4.02 |
|  |  |  |  | 0.1 | 0 | 94.78 ± 28.30 |
| 3 | 2, 8 | AmOH | S | 10.0[g] | + | 1.30 ± 0.84 |
|  |  |  |  | 33.0[g,h] | ++ | 6.07 ± 2.35 |
| 4 | 2, 8 | AmOH | S | 10.0[g] | + | 0.82 ± 0.45 |
|  |  |  |  | 33.0[g,h] | 0 | 0.85 ± 0.59 |
| 5 | 2, 8 | Im | S | 10.0 | 0 | 28.03 ± 12.72 |
| 6 | 2, 8 | Im | SO$_2$ | 10.0 | 0 | 93.48 ± 9.58 |
| 7 | 3, 7 | Am | S | 10.0 | 0 | 35.95 ± 9.59 |
| 8 | 3, 7 | iPrAm | S | 10.0 | + | 0.04 ± 0.02 |
| 9 | 3, 7 | AmOH | S | 10.0[g] | + | 111.64 ± 76.53 |
|  |  |  |  | 33.0[g,h] | 0 | 45.56 ± 26.12 |

[a]All compounds were isolated as the dihydrochloride salt, with exception of 3, which was isolated as the monohemimaleate salt.
[b]Am = group with =NH and NH$_2$; iPrAm = N-isopropyl amidine; AmOH = amidoxime (=NOH, NH$_2$); Im = imidazoline.
[c]Expressed as μmol/kg/day, given iv via tail vain to at least 8 rats once daily for 14 days, unless stated otherwise.
[d]Toxicity scores are subjective evaluations of overt toxicity in dexamethasone immunosuppressed rats. A score of '0' indicates no observable deleterious effects from dosing. A score of '+' indicates slight hypoactivity with compounds 2 and 8, and tail inflammation with compounds 3, 4, and 9. A score of '++' indicates hypoactivity, dyspnea, and ataxia with pentamidine, and chromic toxicity resulting in 2 of 8 animals dead with compound 3.
[e]Cysts/g lung counts were 69.18 (× 10$^6$) for the saline control group and 0.51 (× 10$^6$) for the pentamidine group. These scores were pooled across experiments involving compounds 1–9. Saline: n = 55; pentamidine: n = 52.
[f]Change in melting point determined on calf thymus DNA.
[g]Doses given to 4 rats.
[h]Doses given by oral gavage.
[i]Tested as the ditrifluroacetate salt.

DNA binding

All of the compounds which were active against PCP, except for the amidoxime prodrugs, were bound to calf thymus DNA, as evidenced by a change in thermal melting of at least 5° C. Compounds 1, 2, and 8, which were highly active against PCP, exhibited ΔTm values of 12.4, 6.4, and 14.5° C., respectively. The sulfone 6, which was inactive against PCP, exhibited a ΔTm value of 2.3° C. On the other hand, compounds 5 and 7 were tightly bound to DNA, with ΔTm values of 19.0 and 15.0° C., respectively, but were weakly active or inactive against PCP. While the molecules' ability to bind to DNA was required for anti-PCP activity, no quantitative relationship was observed between anti-PCP activity and the strength of DNA binding.

Biological Studies

The anti-PCP activity of the compounds was determined using a standard procedure (Tidwell, R. R. et al., *Antimicrob. Agents Chemother.* 1993, 37, 1713–1716), as was the binding of the molecules to DNA as determined by thermal melting of calf thymus DNA (Tidwell, R. R. et al., *Antimicrob. Agents Chemother.* 1993, 37, 1713–1716).

C. Experimental Protocols

General experimental. Uncorrected melting points were measured on a Thomas Hoover capillary melting point apparatus or a Mel-Temp II apparatus. IR spectra were recorded in Nujol mulls or KBr pellets on a Perkin-Elmer 1320 spectrophotometer. $^1$H NMR spectra were recorded on Varian XL 400 and Bruker AMX-500 MHz spectrometers. Anhydrous ethanol was distilled over Mg immediately prior to use. Isopropyl amine was distilled over KOH prior to use. Ethanolic solutions of hydroxylamine were prepared by treating solutions of hydroxylamine hydrochloride with equimolar amounts of sodium ethoxide (21% solution in denatured alcohol), and filtering off the resultant sodium chloride. Reaction products were dried over $P_2O_5$ at 77 or 110° C. at 0.2 mm Hg. Unless stated otherwise, reactions were monitored by TLC on silica or by reverse phase HPLC. HPLC chromatograms were recorded as previously described (Patrick, D. A. et al.,. *Eur. J. Med. Chem.* 1997, 32, 781–793) with the following modifications. A Dupont Zorbax Rx C8 column (3.5μ, 3.0 mm×15 cm) was used. Mobile phases consisted of mixtures of acetonitrile (3.75–67.5% v/v) in water containing tetramethylammonium chloride, sodium heptanesulfonate, and phosphate buffer pH 2.5 (10 mM each). In method A the concentration of acetonitrile was maintained at 3.75% for 0.5 min, increased to 45% following a linear gradient over 12.5 min, increased immediately to 67.5% following a linear gradient over 3 min, then maintained at 67.5% for 4.5 min. Method B was identical to method A, except that the acetonitrile concentrations were 5, 47, 68, and 68%, at the respective time points. FAB mass spectra were recorded on a VG 70-SEQ Hybrid spectrometer (cesium ion gun, 30 KV). Microanalyses were performed by Atlantic Microlab, Norcross, Ga., and were within ±0.4% of calculated values. Intermediates 10 and 11 were each prepared in two steps from dibenzothiophene using known procedures (Campaigne, E.; Ashby, J. *J. Heterocyclic Chem.* 1969, 6, 517–522; DuVernet, R. B. et al., *J. Am. Chem. Soc.* 1978, 100, 2457–2464; Brown, R. K. et al., *J. Org. Chem.* 1952, 74, 1165–1167; Ho, T. -L.; Wong, C. M.. *Synthesis* 1972, 561–562). Dibenzothiophene was purchased from Aldrich Chemical Co., Milwaukee, Wis.

General procedure for Pinner syntheses of compounds 1–4 and 7–9.

Method A. A stirred suspension of the dinitrile and anhydrous ethanol in 1,4-dioxane in a 3-neck flask equipped with a hydrogen chloride inlet tube, a thermometer, and a drying tube was cooled in an ice-salt bath. Hydrogen chloride was introduced into the system at such a rate that the temperature of the reaction mixture did not exceed 5° C., until the system was saturated with HCl. The reaction mixture was then tightly stoppered and stirred at room temperature until the nitrile was no longer detectable by IR or HPLC. The reaction mixture was diluted with ether. The crude imidate was filtered off under $N_2$, then reacted immediately with the appropriate amine.

Method B was similar to method A, except that the dioxane was first quickly saturated with hydrogen chloride without regard to temperature. The solution was cooled to 0° C. before the nitrile and the ethanol were added. Hydrogen chloride was passed slowly through the system for 15–30 min to ensure complete saturation.

2,8-Diamidinodibenzothiophene dihydrochloride (1). The imidate was prepared from 2,8-dicyanodibenzothiophene (10, 2.35 g, 10.0 mmol), ethanol (2.98 g, 64.7 mmol) and 1,4-dioxane (150 mL) by method A. After 19 days the crude diimidate (3.66 g, 91.4%) was filtered off under nitrogen and was added to a solution of ammonia (12.48 g, 7.33 mmol) in anhydrous ethanol (100 mL) in a stoppered flask. The mixture was stirred overnight at 40–55° C. The reaction mixture was concentrated, and the crude product was filtered off and washed with ether. The crude product was nearly completely dissolved in hot water (150 mL) and filtered through a layer of Norit-A (4–5 cm thick) over a pad of Celite 545. The filtrate was concentrated to ca. 25 mL. The resultant solid was triturated with ethanol and filtered off. Several crystallizations from acetone-water gave a white powder (0.75 g, 22%): mp>300 C; $^1$H NMR (500 MHz, DMSO-$d_6$) δ 9.50 (br s, 8 H), 9.14 (s, 2 H), 8.39 (d, J=8.4 Hz, 2 H), 8.04 (d, J=8.4 Hz, 2 H); FAB-MS m/z 269 (MH$^+$ of free base); HPLC (method A)$t_R$ 10.48 min (96.2 area %). Anal. ($C_{14}H_{13}N_4S.2HCl.H_2O$) C, H, N.

2,8-Bis(N-isopropylamidino)carbazole dihydrochloride (2). The imidate was prepared from 2,8-dicyanodibenzothiophene (10, 2.36 g, 10.1 mmol), anhydrous ethanol (5.0 mL, 86 mmol), and 1,4-dioxane (200 mL) by method B. The crude imidate (4.30 g, 107%) was filtered off after 27 days. A portion of the crude imidate (2.06 g) was stirred overnight at room temperature in a solution of isopropyl amine (10 mL, 235 mmol) under nitrogen. The resultant precipitate was filtered off to give a white solid (1.10 g, 53.7%): mp>300° C.; $^1$H NMR (500 MHz, DMSO-$d_6$) δ 9.8 (v br s, 6 H), 9.05 (s, 2 H), 8.36 (d J=8.4 Hz, 2 H), 7.94 (d J=8.4 Hz, 2 H), 4.19 (m, 2 H), 1.34 (d, J=6.3 Hz, 12 H); FAB-MS m/z 353 (MH$^+$ of free base); HPLC (method A)$t_R$ 11.80 min (98.6 area %). Anal. ($C_{20}H_{24}N_4S.2HCl.H_2O$) C, H, N, S, Cl.

2,8-Bis(N-hydroxyamidino)carbazole hemimaleate (3). The imidate was prepared from 2,8-dicyanodibenzothiophene (10, 2.36 g, 10.1 mmol), ethanol (5.0 mL, 85 mmol) and 1,4-dioxane (150 mL) by method A. After 29 days the crude imidate (4.77 g, 119%) was filtered off and was stirred at reflux for 6 hours in a solution of hydroxylamine prepared from hydroxylamine hydrochloride (7.15 g, 123 mmol), and sodium ethoxide (37 mL of a 21% solution, 99 mmol) and ethanol (100 mL). The crude product was filtered off and dissolved in ethanolic HCl solution. A precipitate formed upon the addition of ether. A filtered aqueous solution of the solid was treated with 10% $NaHCO_3$ solution to precipitate out the free base. An ethanolic suspension of the solid (0.52 g) was treated with a solution of maleic acid (1.00 g) in ethanol (8 mL). All solids went into solution, and a new precipitate formed as the hemimaleate salt (0.41 g, 4.2%): mp; $^1$H NMR (400 MHz, DMSO-$d_6$) δ 10.10 (br s, 2 H), 8.72 (s, 2 H), 8.11 (d, J=8.5 Hz, 2 H), 7.86 (dd, J=8.4 and 1.6 Hz, 2 H), 6.85 (br s, 3.5 H), 6.13 (s, 2 H); high resolution FAB-MS m/z 301.0753 (calcd m/z 301.0759 for $C_{14}H_{13}N_4O_2S$); HPLC (method A)$t_R$ 10.68 min (92.9 area %). Anal. ($C_{14}H_{12}N_4O_2S.C_4H_4O_4$) C, H, N, S.

2,8-Bis(N-hydroxyamidino)carbazole dihydrochloride (4). The imidate was prepared 2,8-dicyanodibenzothiophene (10, 2.00 g, 8.54 632 mol), ethanol (3.0 mL, 51 mmol) and 1,4-dioxane (120 mL) by method B. After 20 days the crude imidate was filtered off and was stirred at reflux for 6 hours in a solution of hydroxylamine prepared from hydroxylamine hydrochloride (6.09 g, 87.3 mmol), and sodium ethoxide (32 mL of a 21% solution, 85 mmol) and ethanol (85 mL). The crude product was filtered off and washed with ether, then converted to the dihydrochloride salt by treatment with ethanol and ethanolic HCl. The crude dihydrochloride salt was recrystallized from ethanol-ether to give a white solid (1.68 g, 52%): mp>300° C.; $^1$H NMR (300 MHz, DMSO-$d_6$) δ 10.10 (br s, 2 H), 8.81 (d, J=1.4 Hz, 2 H), 8.21 (d, J=8.5 Hz, 2 H), 7.90 (dd, J=8.5 and 1.4 Hz, 2 H), 7.62 (v br s, 3 H), 6.85 (v br s, 4 H); FAB-MS m/z 301 (MH$^+$ of free base); HPLC (method B)$t_R$ 9.93 min (95.4 area %). Anal. ($C_{14}H_{12}N_4O_2S \cdot 2HCl \cdot 2H_2O$) C, H, N, S, Cl.

2,8-Bis(2-imidazolinyl)dibenzothiophene dihydrochloride (5). A slurry of finely pulverized 2,8-dicyanodibenzothiophene (10, 1.78 g, 5.02 mmol), and ethylenediamine dihydrochloride (8.86 g, 66.6 mmol) in ethylenediamine (10 mL, 150 mmol) in a 50 mL beaker was heated at 310° C. in a sand bath for 30 minutes with occasional manual stirring. The reaction mixture was nearly completely dissolved in hot water (ca. 100 mL) and filtered through Celite 545. The filtrate was cooled in an ice bath, then alkalinized with 2 N NaOH solution (75 mL). The free base was filtered off, partially dried, and suspended in hot ethanol (50 mL). The mixture was treated with ethanolic HCl (10 mL), and the undissolved solid was filtered off to give (as the dihydrochloride salt) beige micro crystals (1.41 g, 81%): mp >330° C.; $^1$H NMR (500 MHz, TFA-d) δ 8.96 (s, 2 H), 8.11 (d, J=8.4 Hz, 2 H), 7.90 (d, J=8.4 Hz, 2 H), 4.27 (s, 8 H); $^1$H NMR (400 MHz, DMSO-$d_6$) δ 11.08 (s, 4 H), 9.23 (d J=21.6 Hz, 2 H), 8.42 (d, J=8.5 Hz, 2 H), 8.18 (dd, J=8.4 and 1.6 Hz, 2 H), 4.07 (s, 8 H); m/z 321 (MH$^+$ of free base); HPLC (method A)$t_R$ 11.023 min (95.5 area %). Anal. ($C_{18}H_{16}N_4S \cdot 2HCl \cdot H_2O$) C, H, N, S, Cl.

2,8-Bis(2-imidazolinyl)-5,5-dioxodibenzothiophene dihydrochloride (6). Hydrogen peroxide (5 mL of a 30% solution) was added to a solution of 2,8-bis(2-imidazolinyl)dibenzothiophene dihydrochloride (10, 0.67 g, 1.7 mmol) in trifluoroacetic acid (10 mL). An exothermic reaction resulted. Another portion (5 mL) of the peroxide solution was added, and the mixture was stirred overnight at room temperature. HPLC analysis showed a mixture of the desired product and the purported sulfoxide intermediate. Another portion of the peroxide solution (10 mL) and the reaction was allowed to proceed for a total of 40 h. The reaction mixture was basified with 2 N NaOH solution. The resultant free base (0.53 g, 89% recovery) was filtered off, washed with water, and dried. The solid was nearly completely dissolved in hot ethanol (80 mL) and filtered through Celite 545. The filtrate was concentrated to ca. 40 mL and treated with ethanolic HCl (10 mL) to give ivory crystals (0.51 g, 71%): mp >300° C.; $^1$H NMR (400 MHz, DMSO-$d_6$) δ 11.30 (s, 4 H), 9.05 (s, 2 H), 8.47 (d, J=8.1 Hz, 2 H), 8.31 (dd, J=8.1 and 1.4 Hz, 2 H), 4.09 (s, 8 H); m/z 353 (MH$^+$ of free base); HPLC (method A)$t_R$ 10.09 min (98.3 area %). Anal. ($C_{18}H_{16}N_4O_2S \cdot 2HCl \cdot 0.5H_2O$) C, H, N, Cl.

3,7-Diamidinodibenzothiophene dihydrochloride (7). The imidate intermediate was prepared from 3,7-Dicyanodibenzothiophene (14, 3.52 g, 15.0 mmol), ethanol (10 mL, 170 mmol), and 1,4-dioxane (225 mL) by method B. After 9 days the crude imidate (5.70 g, 96% recovery) was collected. An aliquot (2.87 g) of the crude imidate was added to anhydrous ethanol (63 mL) saturated with ammonia. The solid dissolved and a new precipitate formed. The mixture was stirred overnight at room temperature in a stoppered flask. The crude product was filtered off, suspended in ethanol and treated with ethanolic HCl. Recrystallization from water-isopropyl alcohol gave a white solid (0.63 g, 26%): mp 385–388 C; $^1$H NMR (400 MHz, DMSO-$d_6$) δ 9.65 (s, 4 H), 9.43 (2, 4 H), 8.78 (d, J=8.2 Hz, 2 H), 8.69 (2, 2 H), 8.01 (d, J=8.2 Hz, 2 H); m/z 269 (MH$^+$ of free base); HPLC (method B)$t_R$ 9.16 min (98.1 area %). Anal. ($C_{14}H_{12}N_4S \cdot 2HCl \cdot 0.25H_2O$) C, H, N, S, Cl.

3,7-Bis(N-isopropylamidino)dibenzothiophene dihydrochloride (8). An aliquot (2.87 g) of the crude imidate described above was suspended in ethanol (30 mL) and diluted with isopropyl amine (20 mL, 230 mmol). Solids went into solution, and a precipitate had formed after the mixture had stirred at room temperature overnight. The excess amine was distilled off. The cooled reaction mixture was diluted with ether, and the crude product was filtered off. Recrystallization from water-isopropyl alcohol gave white crystals (1.51 g, 49%); mp 337–338° C.; $^1$H NMR (400 MHz, DMSO-$d_6$) δ 9.86 (d, J=8.3 Hz, 2 H), 9.70 (s, 2 H), 9.37 (s, 2 H), 8.75 (d, J=8.4 Hz, 2 H), 8.59 (s, 2 H), 7.92 (d, J=8.4 Hz, 2 H), 4.16 (m, 2 H), 1.32 (d, J=6.2 Hz, 12 H); m/z 353 (MH$^+$ of free base); HPLC (method B)$t_R$ 11.12 min (95.6 area %). Anal. ($C_{20}H_{24}N_4S \cdot 2HCl$) C, H, N, S, Cl.

3,7-Bis(N-hydroxyamidino)dibenzothiophene dihydrochloride (9). The imidate intermediate was prepared from 3,7-dicyanodibenzothiophene (14, 1.00 g, 4.26 mmol), ethanol (5.5 mL, 94 mmol), and 1,4-dioxane (75 mL) by method B. After 5 days the crude imidate (1.66 g, 97% recovery) was collected and suspended in anhydrous ethanol (15 mL). The suspension was diluted with a solution of hydroxylamine prepared from hydroxylamine (3.5 g, 50 mmol), sodium ethoxide (21% solution in denatured alcohol, 18 mL, 48 mmol), and ethanol (60 mL). Solids went into solution and a new precipitate formed. After 2.5 h the mixture was diluted with ether, and the crude product was filtered off. A suspension of the crude product in water (10 mL) was diluted with 2 N HCl (2–3 mL) until the solid dissolved. The turbid solution was filtered, and the filtrate was diluted with conc. HCl (20 mL). The resultant precipitate was filtered off to give a white solid (0.58 g, 36%): mp>300° C.; $^1$H NMR (400 MHz, DMSO-$d_6$) δ 11.44 (br s, 2 H), 9.20 (br s, 3 H), 8.74 (d, J=8.4 Hz, 2 H), 8.59 (d, J=1.5 Hz, 2 H), 7.91 (dd, J=8.4 and 1.5 Hz, 2 H); high resolution FAB MS m/z 301.0730 (calcd m/z 301.0759 for $C_{14}H_{13}N_4O_2S$); HPLC (method B)$t_R$ 8.87 min (96.4 area %). Anal. ($C_{14}H_{12}N_4O_2S \cdot 2HCl \cdot 0.85H_2O$) C, H, N, S, Cl.

3,7-Diaminodibenzothiophene dihydrochloride (12). 3,7-Dinitro-5-oxo-dibenzothiophene (11, 9.60 g, 33.1 mmol) was hydrogenated in four batches at 45 psi over 10% palladium on carbon in ethanol. In each batch 300 mL of ethanol and 0.4 to 0.5 g of catalyst were used, and the reaction time was 2 h. After each hydrogenation, the catalyst was filtered off, and the filtrate was immediately treated with ethanolic HCl (10–15 mL) to give a white precipitate. The combined precipitates were collected to give white solid (8.68 g, 91.5%): mp 280 C; $^1$H NMR (400 MHz, DMSO-$d_6$) δ 8.36 (d, J=8.4 Hz, 2 H), 7.92 (s, 2 H), 7.42 (dd, J=8.4 and 1.6 Hz, 2H); HPLC (method B)$t_R$ 9.58 min (96.2 area %).

3,7-Dibromodibenzothiophene (13). A suspension of 3,7-diaminodibenzothiophene dihydrochloride (12, 7.32 g, 25.5 mmol) in water (50 mL) and conc. HCl (13 mL) was cooled in an ice-salt bath to 5° C. A solution of sodium nitrite (5.27 g 76.4 mmol) in water (15 mL) was added dropwise at such a rate that the temperature of the reaction mixture did not exceed 110° C. After 45 min the reaction mixture was poured into a solution of copper(I) bromide in 48% HBr (90 mL). The mixture was heated at reflux for 2 h, cooled, and poured into ice-water. (total volume a. 1500 mL). The resultant yellow precipitate was filtered off, dried, and sublimed 168° C., 0.2 mm Hg) to give a pale yellow solid (6.84 g, 78.6%): mp 171–173° C. (lit. (Gerdil, R.; Lucken, E. C.. *J. Am. Chem. Soc.* 1965, 87)[7] 180° C.); $^1$H NMR (400 MHz, CDCl$_3$) δ 7.98 (d, J=1.7 Hz, 2 H), 7.96 (d, J=8.6 Hz, 2 H), 7.58 (dd, J=8.6 and 1.7 Hz, 2 H).

3,7-Dicyanodibenzothiophene (14). A refluxing solution of 3,7-dibromodibenzothiophene (13, 1.56 g, 4.56 mmol) and copper(I) cyanide (1.27 g, 14.2 mmol) in 1-methyl-2-pyrrolidinone (10 mL) was stirred under nitrogen for 3 h. The cooled reaction mixture was treated with a solution of FeCl$_3$ (3.29 g) in conc. HCl (10 mL). After the initial exotherm, the mixture was stirred with heat for 1 h. The mixture was poured over ice. The resultant gray precipitate was filtered off, dried, and sublimed (280° C., 0.3 mm Hg) to give white powder (0.89 g, 84%): mp >330° C.; $^1$H NMR (400 MHz, DMSO-d$_6$) δ 8.76 (s, 2 H), 8.71 (d, J=8.2 Hz, 2 H), 8.01 (dd, J=8.2 and 1.4 Hz, 2 H); HPLC (method B)t$_R$ 16.84 min (93.5 area %). Anal. (C$_{14}$H$_6$N$_2$S.0.25H$_2$O) C, H, N.

D. Microanalysis data (supplemental)

2,8-Diamidinodibenzothiophene dihydrochloride (1).
Anal. Calcd for C$_{14}$H$_{13}$N$_4$S.2HCl.H2O: C, 46.80; H, 4.99; N, 15.59. Found: C, 46.99; H, 4.53; N, 15.46.

2,8-Bis(N-isopropylamidino)carbazole dihydrochloride (2).
Anal. Calcd for C$_{20}$H$_{24}$N$_4$S.2HCl.H$_2$O: C, 56.47; H, 6.16; N, 13.17; S, 7.54; Cl, 16.67. Found: C, 56.24; H, 6.22; N, 12.99; S, 7.32; Cl, 16.44.

2,8-Bis(N-hydroxyamidino)carbazole hemimaleate (3).
Anal. Calcd for C$_{14}$H$_{12}$N$_4$O$_2$S.C$_4$H$_4$O$_4$: C, 91.92; H, 3.87; N, 13.45; S, 7.70. Found: C, 51.89; H, 3.90; N, 13.24; S, 7.57.

2,8-Bis(N-hydroxyamidino)carbazole dihydrochloride (4).
Anal. Calcd for C$_{14}$H$_{12}$N$_4$O$_2$S.2HCl.2H$_2$O: C, 42.98; H, 4.12; N, 14.32; S, 8.19; Cl, 18.12. Found: C, 43.05; H, 4.10; N, 14.17; S, 8.31; Cl, 17.98.

2,8-Bis(2-imidazolinyl)dibenzothiophene dihydrochloride (5).
Anal. Calcd for C$_{18}$H$_{16}$N$_4$S.2HCl.H$_2$O: C, 52.56; H, 4.90; N, 13.62; S, 7.79; Cl, 17.24. Found: C, 52.88; H, 5.26; N, 13.60; S, 7.78; Cl, 17.23.

2,8-Bis(2-imidazolinyl)-5,5-dioxodibenzothiophene dihydrochloride (6).
Anal. Calcd for C$_{18}$H$_{16}$N$_4$O$_2$S.2HCl.0.5H$_2$O: C, 49.78; H, 4.41; N, 12.90; Cl, 16.32. Found: C, 49.78; H, 4.52; N, 12.78; Cl, 16.21.

3,7-Diamidinodibenzothiophene dihydrochloride (7).
Anal. Calcd for C$_{14}$H$_{12}$N$_4$S.2HCl.0.25H$_2$O: C, 48.63; H, 4.23; N, 16.20; S, 9.27; Cl, 20.51. Found: C, 48.91; H, 4.17; N, 15.85; S, 9.31; Cl, 20.33.

3,7-Bis(N-isopropylamidino)dibenzothiophene dihydrochloride (8).
Anal. Calcd for C$_{20}$H$_{24}$N$_4$S.2HCl: C, 56.47; H, 6.16; N, 13.17; S, 7.54; Cl, 16.67. Found: C, 56.45; H, 6.22; N, 13.12; S, 7.55; Cl, 16.61.

3,7-Bis(N-hydroxyamidino)dibenzothiophene dihydrochloride (9).
Anal. Calcd for C$_{14}$H$_{12}$N$_4$O$_2$S.2HCl.0.85H$_2$O: C, 43.27; H, 4.07; N, 14.42; S, 8.25; Cl, 18.25. Found: C, 43.65; H, 4.12; N, 14.05; S, 8.22; Cl, 18.25.

3,7-Diaminodibenzothiophene dihydrochloride (12).
Microanalysis not done.

3,7-Dibromodibenzothiophene (13).
Microanalysis not done.

3,7-Dicyanodibenzothiophene (14).
Anal. Calcd for C$_{14}$H$_6$N$_2$S.0.25H$_2$O: C, 70.42; H, 2.74; N, 11.73. Found: C, 70.39; H, 2.59; N, 11.51.

EXAMPLE 2

Dicationic Dibenzofuran Derivatives as Anti-Pneumocystis cariniiPneumonia

Agents: Synthesis, DNA Binding Affinity, and Anti-*P. carinii* Activity in an Immunosuppressed Rat Model This example contains the synthesis and anti-PCP testing of a series of dicationic dibenzofurans (see structures below) and selected amidoxime derivatives. Because DNA minor groove binding is hypothesized to play a major role in the antimicrobial activity of these molecules [Bell, C. A. et al., *Antimicrob. Agents Chemother.* 1993, 37, 2668–2673; Dykstra, C. C. et al., *J. Protozool.* 1991, 6, 78S-81S; Dykstra, C. C. et al.; *Antimicrob. Agents and Chemother.* 1994, 38, 1890–1898; Cory, M.; et al., *J. Med. Chem.* 1992, 35, 431–438; Fairley, T. et al. *J. Med. Chem.* 1993, 36, 1746–1753; Bell, C. A. et al.; *Antimicrob. Agents Chemother.* 1991, 35, 1099–1107], tests were also performed to determine the binding affinity of the molecules with calf thymus DNA and a poly dA.poly dT oligomer.

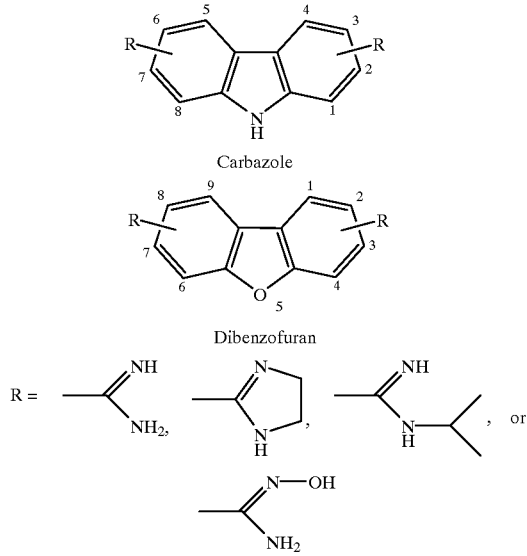

Chemistry

Referring now to Scheme 2, diamidine 1 was first made by Moffatt in 1950 [Moffatt, J. S. 3:6-Diamidinodibenzofuran. *J. Chem. Soc.* 1951, 625–626], while the other dications synthesized in this example are novel. The 2,8-disubstituted dibenzofurans were synthesized from the commercially available dibenzofuran 9. 2,8-Dibromodibenzofuran 10 [Turner, W. R. et al., *J. Med. Chem.* 1985, 28, 1728–1740], the major product of bromination of dibenzofuran 9, underwent nucleophilic reaction with copper(I) cyanide in refluxing N,N-dimethylformamide to provide dicyanodibenzofuran 11 [Turner, W. R. et al., *J. Med. Chem.* 1985, 28, 1728–1740]. The diimidate intermediate 12 was prepared from 11 through Pinner reaction

[Tidwell, R. R. et al., *Ann. NY Acad. Sci.* 1990, 616, 421–441; Pinner, A.; Klein, F. *Chem. Ber.* 1878, 11, 1475–1487; Pinner *Chem. Ber.* 1883, 16, 352–363; Pinner, A. *Chem. Ber.* 1883, 16, 352–363; Chakrabarti, A.; et al., *Tetrahedron* 1989, 45, 5059–5064] by reacting with ethanol in hydrochloride saturated 1,4-dioxane at room temperature for 9–14 days. The diimidate 12 was isolated without being characterized after high conversion was determined by HPLC and IR. The dried diimidate 12 reacted with excess ammonia, ethylenediamine, isopropylamine, and hydroxylamine in anhydrous ethanol to give the final compounds diamidine 1, diimidazoline 2, di(isopropylamidine) 3, and diamidoxime 4 respectively. All these dications were in hydrochloride salt forms after final purification.

condition for obtaining the desired product 15 was temperature control (0° C. at the beginning of the reaction, then increased to room temperature as the reaction slowed). The nitro group of compound 15 was reduced to the corresponding amine 16 using 5% ruthenium on carbon as a catalyst in ethanol at 65–70° C. [Miesel, J. L.; O'Doherty, G. O. P.; Owen, J. M. In *Catalysis in Organic Chemistry.*; Rylander, Ed.; Academic Press: New York, 1976; pp 273–285.]. The dibenzofaran ring was formed with minor modifications of a reported procedure [Erdtman, H. et al., *Acta. Chem. Scand.* 1961, 15, 1761–1764]. The amino group in compound 16 was first diazotized in sodium nitrite and sulfuric acid aqueous solution. The diazonium salt 17 was heated to reflux in situ to give 3,7-dibromodibenzofuran 18. The 3,7-

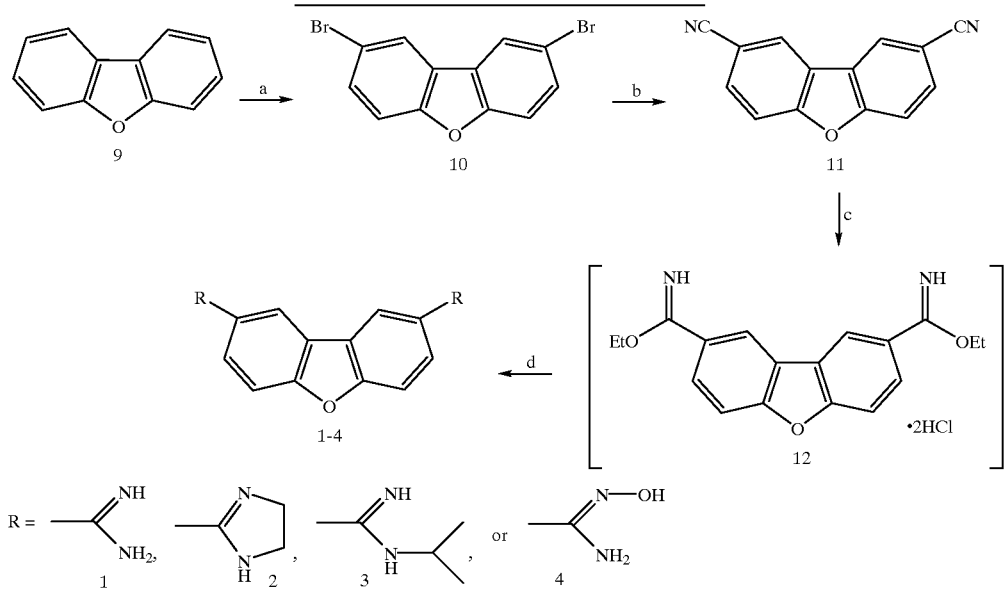

Scheme 2
Synthesis of 2,8-disubstituted dibenzofuran dications[a]

[a]Key: (a) Br2/AcOH/reflux; (b) CuCN/DMF/reflux; (c) EtOH/1,4,-dioxane/room temperature; (d) appropriate amine/EtOH.

3,7-Disubstituted dibenzofuran derivatives (Scheme 3) could not be synthesized effectively from the dibenzofuran ring. Therefore, de novo furan ring preparation was necessary to obtain the desired products. Ullman coupling reaction [Yamato, T.; et al.,*J. Org. Chem.* 1991, 56, 6248–6250] of 2,5-dibromonitrobenzene 13 with copper powder in N,N-dimethylformamide at 120° C. gave compound 14. Selective nucleophilic substitution of 14 by reacting with sodium methoxide between 0° C. and room temperature provided the methoxy compound 15. Since the aromatic nitro group is a better leaving group than the aromatic bromo group, selective substitution could be achieved [Beck, J. R. et al., *J. Org. Chem.* 1974, 39, 18391841; Effenberger, F. et al., *Chem. Ber.* 1991, 124, 163–173]. However, significant impurities were found in the reaction mixture, resulting from different combinations of methoxy substitution. The key dicyanodibenzofuran 19 was prepared from 18, by reacting with copper (I) cyanide in refluxing N,N-dimethylformamide. Pinner reaction [Tidwell, R. R. et al., *Ann. NY Acad. Sci.* 1990, 616, 421–441; Pinner, A.; Klein, F. *Chem. Ber.* 1878, 11, 1475–1487; Pinner *Chem. Ber.* 1883, 16, 352–363; Pinner, A. *Chem. Ber.* 1883, 16, 352–363; Chakrabarti, A.; et al., *Tetrahedron* 1989, 45, 5059–5064] of compound 19 with ethanol in HCl saturated 1,4-dioxane at room temperature for 2 weeks gave the intermediate 3,7-diimidatedibenzofuran 20, which was isolated without characterization. 20 was reacted with either excess ammonia, ethylenediamine, isopropylamine, or hydroxylamine in ethanol solution to give corresponding diamidine 5, diimidazoline 6, di(isopropylamidine) 7, or diamidoxime 8.

Scheme 3
Synthesis of 3,7-disubstituted dibenzofuran dications.[a]

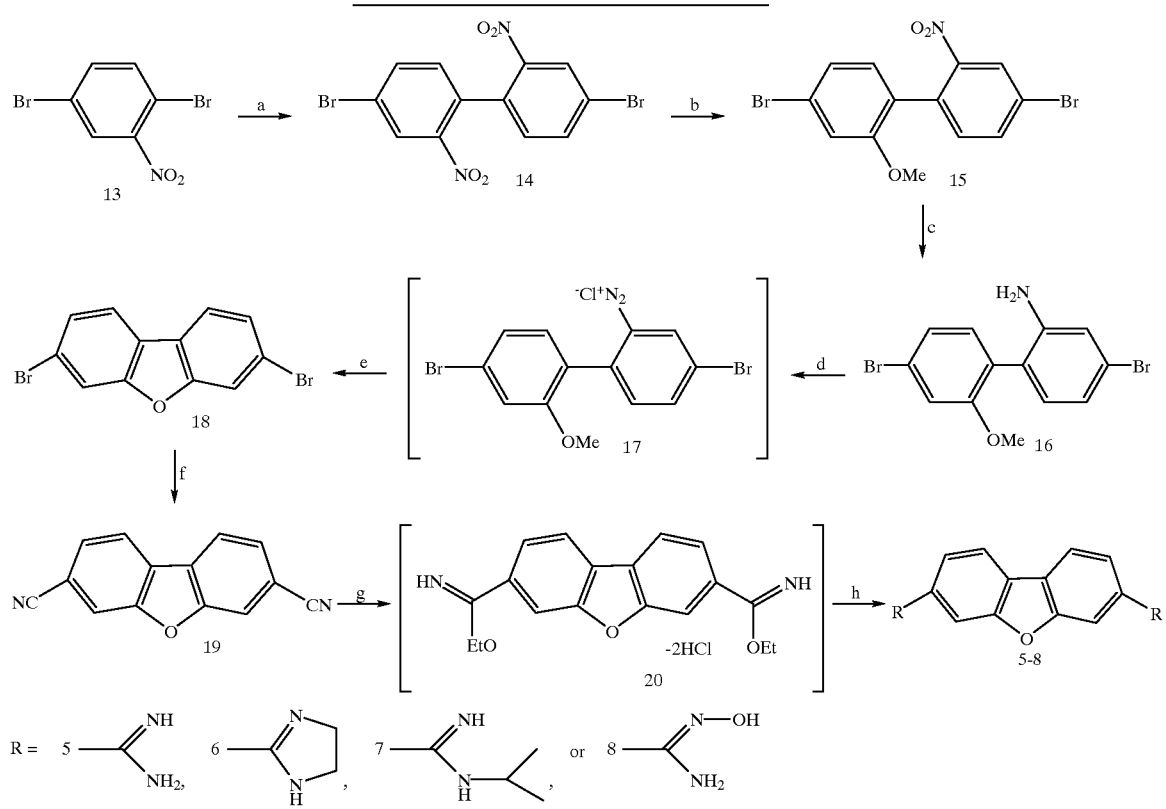

[a]Key: (a) Cu/DMF/120° C.; (b) NaOMe/MeOH/DMF; (c) NH2NH2·H20/5%Ru/C/EtOH; (d) NaNO2/H2SO4/<5° C.; (e) Reflux; (f) CuCN/DMF/reflux; (g) EtOH/HCl/1,4-dioxane; (h) Appropriate amine/EtOH.

Results and Discussion

Activity against *P. carinii* pneumonia

The activity of compounds 1–8 against PCP in the rat model is shown in Table 2. Compounds 1–3 and 5–7 in the initial screen were given once daily by tail vein injection at a dose of 10 μmol/kg/day for 14 days, with activities compared to pentamidine at approximately one-half the effective iv dose of pentamidine, which is 22 μmol/kg/day. Two of the six dicationic compounds (3 and 7) were found to be highly potent at the screening dose, reducing the parasite load by over 99%. Both highly active compounds contained isopropyl substituted diamidines, with the cationic moieties of 3 located para and those of 7 meta to the faran oxygen atom. The 2,8-diamidine 1 was found to be comparable in activity to pentamidine at its screening dose and more active than pentamidine when given at the same dose as pentamidine. In contrast, the 3,7-diamidine 5 was found to be inactive. The 2,8-diimidazoline 2 and 3,7-diimidazoline 6 were both inactive at the screening dose.

The observed toxicities of compounds 1–3 and 5–7 were found to be less than or equivalent to that of pentamidine at the doses used.

Compounds 4 and 8 were synthesized to test if diamidoximes would be effective prodrugs of the dibenzofuran diamidines. Both the diamidoximes were screened for anti-*P. carinii* activity at 10 μmol/kg/day by tail vein injection and 33 μmol/kg/day by oral gavage for 14 days. The diamidoximes 4 and 8 were compared for efficacy with pentamidoxime, an effective prodrug. Not surprisingly, 3,7-diamidoxime 8 was not active since the corresponding diamidine 5 was not active. Compound 4 had only moderate activity against PCP, while the corresponding diamidine 1 proved to be potent. Further studies of diamidoxime metabolism are being performed using cultured cell lines and cell-free enzyme preparations to understand more about the metabolic mechanisms of prodrug activation. Preliminary results showed that the conversion of 2,8-dibenzofuran diamidoxime to diamidine is less efficient than conversion of pentamidoxime to pentamidine by whole cells.

TABLE 2

Activity against *Pneumocystis carinii* pneumonia (PCP) by dibenzofuran dications.

[Structure: dibenzofuran with R₁ at position 8/7 and R₂ at position 2/3, with oxygen at bottom]

| Compound | Position of $R_1$, $R_2$ | $R_1$ | $R_2$ | Dose[a] | Toxicity[b] | *Pneumocystis carinii* % Saline control ± std error[c] |
|---|---|---|---|---|---|---|
| Pentamidine | — | — | — | 22.0 | ++ | 0.80 ± 0.17 |
| Pentamidoxime | — | — | — | 22.0 | + | 0.11 ± 0.02 |
|  |  |  |  | 33.0* | 0 | 13.76 ± 9.12 |
| 1 | 2, 8 | Am | Am | 10.0 | + | 7.15 ± 3.81 |
|  |  |  |  | 22.0 | ++ | 0.10 ± 0.02 |
| 2 | 2, 8 | Im | Im | 10.0 | + | 97.36 ± 31.92 |
| 3 | 2, 8 | iPrAm | iPrAm | 10.0 | + | 0.50 ± 0.27 |
| 4 | 2, 8 | AmOH | AmOH | 10.0 | + | 15.76 ± 14.60 |
|  |  |  |  | 33.0* | 0 | 45.06 ± 21.61 |
| 5 | 3, 7 | Am | Am | 10.0 | + | 182.65 ± 38.32 |
| 6 | 3, 7 | Im | Im | 10.0 | + | 219.93 ± 39.28 |
| 7 | 3, 7 | iPrAm | iPrAm | 10.0 | + | 0.28 ± 0.27 |
| 8 | 3, 7 | AmOH | AmOH | 10.0 | + | 165.58 ± 108.73 |
|  |  |  |  | 33.0* | 0 | 150.39 ± 54.05 |

[Structures of substituent groups: Am = amidine (C(=NH)NH₂); iPrAm = N-isopropyl amidine; AmOH = hydroxyamidine (C(=NOH)NH₂); Im = imidazoline]

[a]Dose units were μmol/kg/day. Each compound was administered to 8 rats once daily for 14 days. Doses marked with (*) were by oral gavage, all others were i.v. via tail vein.
[b]Toxicity scores were subjective evaluations of overt toxicity in dexamethasone immunosuppressed rats. A score of "0" indicates no observable deleterious effects from dosing, whereas "++" indicates hypotension, ataxia, and dyspnea.
[c]Cysts/g lung counts for the saline and pentamidine control groups were pooled across experiments. Scores for each compound were reported as % of the pooled saline scores. Saline: 47.53 × 10⁶ cysts/g lung (n = 45). Petamidine: 0.38 × 10⁶ cysts/g lung (n = 42).

DNA binding

Previous studies with dicationic carbazoles indicated that carbazoles with the cations substituted meta to the ring heterocycle (2,7-substituted carbazole) bound to the DNA minor groove in a different orientation from carbazoles with the cations para to the ring nitrogen (3,6-disubstituted carbazoles) [Tanious, F. A. et al., *Biochem.* 1997, 36, 15315–15325]. As an example, 3,6-di(2-imidazolinyl) carbazole bound in the minor groove via hydrogen bonds from the two imidazoline groups resulting in an orientation with the ring nitrogen pointing away from the DNA surface. The corresponding 2,7-disubstituted compound was only able to establish two hydrogen bonds with the surface of the minor groove by flipping over and forming hydrogen bonds with the DNA through one of the imidazoline groups and the ring nitrogen. It was anticipated that the 3,7-dicationic benzofurans (cations meta to ring oxygen) would correspond with the 2,7-disubstituted carbazoles in orientation relative to the DNA surface, and therefore, without the hydrogen bond contributed by the ring nitrogen of the carbazole, would be less potent DNA binders than the corresponding 2,7-disubstituted carbazoles. Comparing the DNA binding results in Table I with previous results from the carbazole study indicate only a modest reduction in the $^oT_m$s of dibenzofurans compared to the carbazoles. Furthermore, judging from the carbazole studies it was anticipated that the 2,8-disubstituted dibenzofurans (two hydrogen bond donors) would have highly increased DNA binding potency than the corresponding 3,7-disubstituted dibenzofurans (one hydrogen bond donor). As can be seen from Table I, the 3,7-disubstituted dibenzofurans were found to have $^oT_m$s in the same range as the 2,8-disubstituted analogues.

Another interesting and unexpected result from the DNA binding studies was the relatively low affinity for poly dA.poly dT exhibited by two of the molecules (Compounds 3 and 7). While these two molecules exhibited good affinity for calf thymus DNA, they were found to have low affinity for poly dA.poly dT. Both compounds had isopropyl-substituted amidines as the cationic groups and were potent anti-*P. carinii* agents. The large differential observed between binding calf thymus DNA and poly dA.poly dT for these molecules may represent a different mode of binding as a result of GC base pair interactions. Since the combination of strong DNA affinity and low poly dA.poly dT appears to correlate with potent anti-*P. carinii* activity this would be an exciting area for future study.

Biological studies

The activity of these compounds against *P. carinii* pneumonia in the rat model was determined using a standard procedure [Tidwell, R. R.; Bell, C. A. In *Pneumocystis carinii Pneumonia: Second Edition, revised and expanded.*; P. D. Walzer, Ed.; Marcel Dekker, Inc.: New York, 1993; pp 561–583]. The binding affinities of the compounds with calf thymus DNA and poly dA.poly dT were measured by thermal melting experiments as reported [Tanious, F. A. et al., *Biochem.* 1997, 36, 15315–15325].

Experimental protocol

Uncorrected melting points were measured on a Thomas Hoover capillary melting point apparatus. IR spectra were recorded in Nujol mulls or KBr pellets on a Perkin-Elmer 1320 spectrophotometer. $^1$H NMR and $^{13}$C NMR were recorded on Bruker AC 300, Varian XL 400, and Bruker AMX 500 spectrometers. Chemical shifts were expressed in parts per million relative to tetramethylsilane (TMS) or sodium 3-(trimethylsilyl)propionate. Anhydrous ethanol was distilled over Mg (with trace $I_2$) immediately before use. Reaction products were dried over $P_2O_5$ at room temperature, 40° C. or 77° C. at 0.2 mm Hg. Unless stated otherwise, reactions were monitored by TLC on silica gel or by reverse phase HPLC. HPLC chromatograms were recorded on a Hewlett-Packard 1090 chromatograph using UV detection (230 nm). Chromatographic data were recorded and analyzed with a Hewlett-Packard 3396 integrator. Mobile phase consisted of mixtures of acetonitrile in water containing 10 mM tetramethylammonium chloride, 10 mM sodium heptanesulfonate, and 2.2 mM phosphoric acid (Method 1 and 2) or 10 mM potassium phosphate (Method 3 and 4). HPLC method 1 employed a Dupont Zorbax Rx-$C_8$ column (5.0μ, 4.6 mm×25 cm) with a flow rate of 1.5 ml/min. The concentration of acetonitrile was maintained at 3.75% from 0 to 0.5 min, increased to 45% following a linear gradient in 19.5 min, increased to 67.5% following a linear gradient over 5 min, then maintained at 67.5% for 7 min. HPLC methods 2, 3, and 4 employed a Dupont Zorbax SB-$C_8$ column (3.5μ, 3.0 mm×15 cm) with a flow rate of 0.6 ml/min. In methods 2 and 3, the concentration of acetonitrile was maintained at 3.75% from 0 to 0.5 min, increased to 45% following a linear gradient in 13 min, immediately increased to 67.5% following a linear gradient over 3 min, then maintained at 67.5% for 4.5 min. In method 4, the concentration of acetonitrile was maintained at 5% from 0 to 0.5 min, increased to 47% following a linear gradient in 13 min, immediately increased to 72.5% following a linear gradient over 3 min, then maintained at 72.5% for 4.5 min. Electron impact mass spectra were recorded on a VG 70-SE or a VG 70-SEQ Hybrid spectrometer. FAB mass spectra were recorded on a VG 70-SEQ Hybrid spectrometer (Cesium ion gun, 30 KV). Microanalyses were performed by Atlantic Microlab, Norcross, Ga., and all were within ±0.4% of the theoretical values. Compounds 9 and 13 were purchased from Aldrich Chemical Co., Milwaukee, Wis.

2,8-Diamidinodibenzofuran dihydrochloride 1. A stirred suspension of 2,8-dicyanodibenzofuran (11, 2.07 g, 9.50 mmol) in anhydrous EtOH (3.5 mL, 60 mmol) and 1,4-dioxane (100 mL) was cooled in ice-salt bath and saturated with dry HCl gas at such a rate that the reaction temperature was maintained below 5° C. The flask was then tightly sealed and the mixture was maintained at room temperature for 2 wk, until no or only a small nitrile band (2230 cm$^{-1}$) was detected by IR analysis, and no starting material was detected by HPLC. The reaction mixture was purged with dry $N_2$ gas and diluted with ether (100–200 mL). The crude diimidate was filtered off and dried under $N_2$, and then added immediately to a solution of ethanolic ammonia (50 mL). The resultant suspension was stirred at 50–60° C. overnight in a tightly stoppered flask. The crude product was filtered off and recrystallized several times from water-acetone to give white powder (1.96 g, 63.3%): mp >300° C. [Lit. [Moffatt, J. S. 3:6-Diamidinodibenzofuran. *J. Chem. Soc.* 1951, 625–62]>320° C.]; HPLC method 4 $t_R$=9.48 min (98.1 area %); $^1$H NMR (300 MHz, DMSO-$d_6$) δ 9.64 (s, 4 H), 9.38 (s, 4 H), 8.79 (s, 2 H), 8.09 (s, 4 H); $^{13}$C NMR (75 MHz, DMSO-$d_6$): δ 165.5, 158.7, 128.8, 123.9, 123.0, 122.3, 112.7; FAB-MS m/z 253 (MH$^+$ of free base). Anal. ($C_{14}H_{12}N_4O.2HCl.1.5H_2O$) C, H, N.

2,8-Di(2-imidazolinyl)dibenzofuran dihydrochloride 2. A stirred suspension of 2,8-dicyanodibenzofuran (11, 2.06 g, 9.46 mmol) in anhydrous EtOH (10.0 mL, 170 mmol) and 1,4-dioxane (300 mL) was saturated with dry HCl gas as described above. The crude diimidate was collected after 3 wk. A mixture of half of the diimidate and ethylene diamine (22.74 g, 278.5 mmol) in anhydrous ethanol (80 mL) was refluxed under $N_2$ for 5.5 h. The reaction mixture was passed through decolorizing carbon (1 cm thick), and the filtrate was evaporated. The residue was further purified several times by recrystallization from 3 N HCl-acetone to give a white powder (0.33 g, 17%): mp 299–302° C. (dec.); HPLC method 1 $t_R$=14.65 min (100 area %); $^1$H NMR (500 MHz, DMSO-$d_6$) δ 3.87 (s, 8 H), 7.96 (d, J=8.6 Hz, 2 H), 8.14 (d, J=8.6 Hz, 2 H), 8.77 (s, 2 H); FAB-MS m/z 305 (MH$^+$ of free base). Anal. ($C_{18}H_{16}N_4O_2HCl.1.4H_2O$) C, H, N.

2,8-Di(N-isopropylamidino)dibenzofuran dihydrochloride 3. A stirred suspension of 2,8-dicyanodibenzofuran (11, 2.00 g, 9.17 mmol) in anhydrous EtOH (4.3 mL, 73 mmol) and 1,4-dioxane (100 mL) was saturated with dry HCl gas as described above. The crude diimidate was collected after 2 wk. A mixture of the diimidate and freshly distilled (KOH) isopropylamine (10 mL, 120 mmol) in ethanol (20 mL) was stirred at room temperature for 4 d. The crude product was filtered off and was recrystallized several times from water-acetone to give a pale yellow powder (1.58 g, 42.0%): mp 279–282° C.; HPLC method 3 $t_R$=11.34 min (97.4 area %); $^1$H NMR (300 MHz, DMSO-$d_6$) δ 9.86 (d, J=7.6 Hz, 2 H), 9.69 (s, 2 H), 9.33 (s, 2 H), 8.70 (d, J=1.7 Hz, 2 H), 8.06 (d, J=8.7, 2 H), d 7.98 (dd, $J_1$=8.7 Hz, $J_2$=1.7 Hz, 2 H), 4.18 (m, 2 H), 1.33 (m, 12 H); FAB-MS m/z 337 (MH$^+$ of free base). Anal. ($C_{20}H_{24}N_4O.2HCl.0.90H_2O$) C, H, N, Cl.

2,8-Di(N-hydroxylamidino)dibenzofuran dihydrochloride 4. A stirred suspension of 2,8-dicyanodibenzofuran (11, 3.38 g, 15.5 mmol) in anhydrous EtOH (7.5 mL, 170 mmol) and 1,4-dioxane (110 mL) was saturated with dry HCl gas as described above. The crude diimidate was collected after 2 wk. The crude diimidate was stirred overnight at 40° C. in a solution of hydroxylamine, prepared from hydroxylamine hydrochloride (8.62 g, 124 mmol) and sodium ethoxide (21 wt %, 46.3 mL, 124 mmol) in anhydrous ethanol (100 mL). The reaction mixture was filtered through Celite 545 and the filtrate was diluted with ether. The resultant precipitate was filtered off and was recrystallized several times from 3–6 N HCl-acetone to give a white solid (0.55 g, 10%): mp 300–305° C.; HPLC method 2 $t_R$=9.86 (100 area %); $^1$H NMR (400 MHz, DMSO-$d_6$) δ 13.22 (br s, 1 H), 11.39 (br s, 2 H), 9.13 (br s, 4 H), 8.69 (d, J=1.7 Hz, 2 H), d 8.06 (d, J=8.7 Hz, 2 H), d 7.99 (dd, $J_1$=8.7 Hz, $J_2$=1.7 Hz, 2 H); $^{13}$C NMR (75 MHz, DMSO-$d_6$): δ 157.91, 157.82, 128.09, 123.04, 122.53, 121.52, 112.53; FAB-MS m/z 285 (MH$^+$ of free base). Anal. ($C_{14}H_{12}N_4O_3.2HCl.0.85H_2O$) C, H, N.

3,7-Diamidinodibenzofuran dihydrochloride 5. A stirred suspension of 3,7-dicyanodibenzofuran (19, 2.20 g, 10.1 mmol) in anhydrous EtOH (4.6 mL, 81 mmol) and 1,4-dioxane (100 mL) was saturated with dry HCl gas as described above. The crude diimidate was collected after 2 wk. A mixture of half of the diimidate and ethanolic ammonia solution (80 mL) was stirred at 50–60° C. overnight. The crude product was filtered off, and dilution of the filtrate with ether resulted in further precipitation of product. The combined solids were recrystallized several times from 1 N HCl-acetone to give an off-white powder (0.33 g, 18%): mp>300° C.; HPLC method 3 $t_R$=9.06 min (99.9 area %); $^1$H NMR (300 MHz, DMSO-$d_6$) δ 9.70 (s, 4 H), 9.48 (s, 4 H), 9.56 (d, J=8.2 Hz, 2 H), 8.44 (s, 2 H), 8.00 (d, J=8.2 Hz, 2 H); FAB-MS m/z 253 (MH$^+$). Anal. ($C_{14}H_{12}N_4O.2HCl$) C, H, N, Cl.

3,7-Di(2-imidazolinyl)dibenzofuran dihydrochloride 6. A stirred suspension of 3,7-dicyanodibenzofuran (19, 2.20 g, 10.1 mmol) in anhydrous EtOH (4.6 mL, 81 mmol) and 1,4-dioxane (100 mL) was saturated with dry HCl gas as described above. The crude diimidate was collected after 2 wk. A mixture of half of the diimidate and ethylene diamine (2.02 mL, 30.2 mmol) in ethanol (80 mL) was refluxed overnight under nitrogen. The crude product was filtered off, and recrystallized from 1 N HCl-acetone to give a white solid (0.55 g, 29%): mp >300° C.; HPLC method 3 $t_R$=9.61 min (95.3 area %); $^1$H NMR (300 MHz, TFA-d) δ 4.26 (s, 8 H), 7.86 (d, J=8.2 Hz, 2 H), 8.17 (s, 2 H), 8.28 (d, J=8.2 Hz, 2 H), 11.50 (s, 4 H); FAB-MS m/z 305 (MH$^+$). Anal. ($C_{18}H_{16}N_4O_2HCl.0.30H_2O$) C, H, N, Cl.

3,7-Di(isopropylamidino)dibenzofuran dihydrochloride 7. A stirred suspension of 3,7-dicyanodibenzofuran (19, 1.00 g, 4.58 mmol) in anhydrous EtOH (2.2 mL, 37 mmol) and 1,4-dioxane (80 mL) was saturated with dry HCl gas as described above. The crude diimidate was collected after 2 wk. A mixture of the diimidate and freshly distilled (KOH) isopropylamine (3.1 mL, 37 mmol) in ethanol (20 mL) was stirred at room temperature for 2 d. The crude product was filtered off, and dilution of the filtrate with ether resulted in further precipitation of product. The combined solids were recrystallized from water-acetone to give a pale yellow solid (1.21 g, 64.8%): mp >300° C.; HPLC method 3 $t_R$=10.86 min (95.9 area %); $^1$H NMR (300 MHz, DMSO-d$_6$) δ 9.54 (br s, 6 H), 8.51 (d, J=8.1 Hz, 2 H), 8.27 (s, 2 H), 7.86 (dd, $J_1$=8.1 Hz, $J_2$=1.0 Hz, 2 H), 4.14 (mn, 2 H), 1.32 (d, J=6.3 Hz, 12 H); FAB-MS m/z 337 (MH$^+$). Anal. ($C_{20}H_{24}N_4O_2HCl.0.30H_2O$) C, H, N, Cl.

3,7-Di(A-hydroxylamidino)dibenzofuran dihydrochloride 8. A stirred suspension of 3,7-dicyanodibenzofuran (19, 2.00 g, 9.17 mmol) in anhydrous EtOH (4.2 mL, 73 mmol) and 1,4-dioxane (100 mL) was saturated with dry HCl gas as described above. The crude diimidate was collected after 2 wk. A mixture of the crude diimidate in a solution of hydroxylamine, prepared from hydroxylamine hydrochloride (5.095 g, 73.32 mmol) and sodium ethoxide (21 wt. %, 27.4 mL, 73.3 mmol) in anhydrous ethanol (100 mL) was stirred at 40–50° C. overnight. The crude product was filtered off and recrystallized several times from 1 N HCl-acetone to give a white solid (0.38 g, 12%): mp >300° C.; HPLC method 3 $t_R$=8.83 min (99.6 area %); $^1$H NMR (300 MHz, DMSO-d$_6$) δ 11.3–11.6 (br s, 2 H), 8.8–9.6 (br s, 4 H), 8.51 (d, J=8.4 Hz, 2 H), 8.29 (s, 2 H), 7.89 (d, J=8.4 Hz, 2 H); FAB-MS m/z 285 (MH$^+$). Anal. ($C_{14}H_{12}N_4O_3.2HCl.0.30H_2O$) C, H, N, Cl.

2,8-Dicyanodibenzofuran 11. A mixture of 2,8-dibromodibenzofuran (10, 10.93 g, 33.53 mmol) and copper (I) cyanide (8.91 g, 102 mmol) in DMF (80 mL) was refluxed under N$_2$ for 9 h. The reaction mixture was poured into ice-water (300 mL). The precipitated solid was filtered off and stirred overnight in a solution of ethylenediamine (50 mL) in water (300 mL). The solid was filtered off, washed with water, then stirred in 10% sodium cyanide solution (100 mL) overnight. The solid was further purified by suspension in hot ethanol (100 mL) to give a white powder (6.97 g, 95.2%): mp 298–300° C. (dec.) (Lit. [37] 299° C.); HPLC method 1 $t_R$=24.07 min (97.3 area %); $^1$H NMR (400 MHz, DMSO-d$_6$) δ 8.05 (d, J=8.7 Hz, 2 H), 8.12 (dd, $J_1$=8.7 Hz, $J_2$=1.4 Hz, 2 H), 8.85 (d, J=1.4 Hz, 2 H). Anal. ($C_{14}H_6N_2O.0.4H_2O$) C, H, N.

4,4'-Dibromo-2,2'-dinitrobiphenyl 14 [Moffatt, J. S. 3:6-Diamidinodibenzofuran. J. Chem. Soc. 1951, 625–62]. A suspension of 2,5-dibromonitrobenzene (13, 50.0 g, 178 mmol) and copper powder (100 mesh, 25.0 g, 391 mmol) in DMF (300 mL) was stirred at 137° C. (oil bath) under N$_2$ for 2 h. The mixture was poured into toluene (1000 mL) and stirred for 4 h. Then the mixture was passed through Celite 545. The filtrate was collected and washed with water and dried over anhydrous sodium sulfate. The solvent was evaporated, and the residue was recrystallized from ethanol (650 mL) to give a pale yellow solid (31.33 g, 87.57%): m.p. 143–146° C. (reported 150° C. [Shaw, F. R.; J. Chem. Soc. 1932, 285–297] and 146–148° C. [Yamato, T.; et al., J. Org. Chem. 1991, 56, 6248–6250]); HPLC method 3 $t_R$=18.70 min (97.2%); NMR (300 MHz, CDCl$_3$) δ 8.40 (d, J=2.0 Hz, 2 H), 7.85 (dd, $J_1$=8.2 Hz, $J_2$=2.0 Hz, 2 H), 7.18 (d, J=8.2 Hz, 2 H).

2-Methoxy-2'-nitro-4,4'-dibromobiphenyl 15. A solution of sodium methoxide in methanol (22.7 mL, 99.4 mmol) was added dropwise to a solution of 4,4'-dibromo-2,2'-dinitrobiphenyl (14, 33.28 g, 82.79 mmol) in DMF (250 mL) cooled in ice-bath. The reaction mixture was stirred overnight at room temperature under N$_2$. The reaction mixture was then poured into ice-water (700 mL). The precipitated solid was collected and recrystallized from acetonitrile (200 mL) and methanol (100 mL) to give an olive green crystal (18.88 g, 59.0%): mp 127–129° C.; HPLC method 3 $t_R$=9.57 min (96.5 area %); $^1$H NMR (400 MHz, CDCl$_3$) δ 3.69 (s, 3 H), 7.04 (d, J=1.6 Hz, 1 H), 7.14 (d, J=8.1 Hz, 1 H), 7.23 (dd, $J_1$=1.6 Hz, $J_2$=7.3 Hz, 1 H), 7.26 (d, J=7.3 Hz, 1 H), 7.76 (dd, $J_1$=1.9 Hz, $J_2$=8.1 Hz, 1 H), 8.09 (d, J=1.9 Hz, 1 H); EI-MS m/z 385 (M$^+$). Anal. ($C_{13}H_9O_3NBr_2$) C, H, N.

2-Methoxy-2'-amino-4,4'-dibromobiphenyl 16. A solution of hydrazine hydrate (19.4 mL, 400 mmol) in ethanol (20 mL) was added dropwise into a suspension of 2-methoxy-2'-nitro-4,4'-dibromobiphenyl (15, 25.77 g, 66.59 mmol) and 5% Ru/C (2.69 g, 1.33 mmol) in ethanol (250 mL) maintained at 65–70° C. The reaction mixture was then refluxed for 7 h. The hot reaction mixture was passed through Celite 545 (1 cm thick), and the filtrate was evaporated to give an off-white powder (22.69 g, 95.46%): mp 94.5–97° C.; HPLC method 3 $t_R$=18.57 min (97.9 area %); $^1$H NMR δ 3.40 (br s, 2 H), 3.80 (s, 3 H), 6.9–7.2 (m, 6 H); EI-MS m/z 355 (M$^+$). Anal. ($C_{13}H_{11}ONBr_2$) C, H, N.

3,7-Dibromo-dibenzofuran 18. A solution of sodium nitrite (4.17 g, 60.5 mmol) in water (55.7 mL) was added slowly to a suspension of 2-methoxy-2'-amino-4,4'-dibromobiphenyl (16, 21.60 g, 60.50 mmol) in H$_2$SO$_4$ (14.82 g, 151.3 mmol) in water (52.7 mL), maintained below 2° C. The mixture was stirred for 2 h at 0° C., and then excess urea was added to destroy the unreacted nitrous acid. The reaction mixture was stirred overnight at room temperature, then overnight at 70° C. The solid formed was collected and recrystallized from benzene (120 mL) and methanol (100 mL) to give a beige solid (10.27 g, 52.09%): mp 199–200.5° C.; HPLC method 3 $t_R$=20.99 min (100 area %); $^1$H NMR (300 MHz, CDCl$_3$) δ 7.78 (d, J=8.2 Hz, 2 H), 7.74 (d, J=1.2 Hz, 2 H), 7.49 (dd, $J_1$=8.2 Hz, $J_2$=1.2 Hz, 2 H); EI-Ms m/z 324 (M$^+$). Anal. ($C_{12}H_6OBr_2$) C, H, N.

3,7-Dicyano-dibenzofuran 19. A suspension of 3,7-dibromo-dibenzofuran (18, 10.27 g, 31.51 mmol) and copper(I) cyanide (8.23 g, 94.5 mmol) in DMF (80 mL) was refluxed under N$_2$ for 6 h. The reaction mixture was poured into ice-water (300 mL). The precipitated solid was collected and stirred for 5 h in a solution of ethylenediamine (50 mL) in water (300 mL). The solid was filtered off, washed with water, then stirred in 10% sodium cyanide solution (100 mL) for 4 h. The solid was further purified by suspension in hot ethanol (100 mL) to give a pale yellow powder (6.69 g, 97.43%): mp 322–325° C. (dec.); HPLC method 3 $t_R$=16.56 min (96.6 area %); $^1$H NMR (300 MHz, DMSO-d$_6$) δ 8.51 (d, J=8.3 Hz, 2 H), 8.48 (s, 2 H), 7.95 (dd, $J_1$=8.3 Hz, $J_2$=1.0 Hz, 2 H); EI-MS m/z 218 (M$^+$). Anal. ($C_{14}H_6N_2.0.23H_2O$) C, H, N.

Analyses 2,8-Diamidinodibenzofuran dihydrochloride 1.

$C_{14}H_{12}N_4O.2HCl.1.5H_2O$: calculated C 47.47%, H 4.86%, N 15.91%, Cl 20.13%; found C 47.72%, H 4.95%, N 15.77%, Cl 19.97%.

2,8-Di(2-imidazolinyl)dibenzofuran dihydrochloride 2.

$C_{18}H_{16}N_4O.2HCl.1.4H_2O$: calculated C 53.71%, H 5.27%, N 13.92%; found C 53.74%, H 5.30%, N 13.76%.

2,8-Di(N-isopropylamidino)dibenzofuran dihydrochloride 3.

$C_{20}H_{24}N_4O.2HCl.0.90H_2O$; calculated: C 56.45%, H 6.58%, N 13.16%, Cl 16.66%; found C 56.38%, H 6.60%, N 13.16%, Cl 16.52%.

2,8-Di(N-hydroxylamidino)dibenzofuran dihydrochloride 4.

$C_{14}H_{12}N_4O_3.2HCl.0.85H_2O$; calculated C 45.14%, H 4.25%, N 15.04%; found C 45.47%, H 4.65%, N 15.00%.

3,7-Diamidinodibenzofuran dihydrochloride 5.

$C_{14}H_{12}N_4O.2HCl$: calculated C 51.71%, H 4.34%, N 17.23%, Cl 21.80%; found C 51.66%, H 4.39%, N 17.24%, Cl 21.72%.

3,7-Di(2-imidazolinyl)dibenzofuran dihydrochloride 6.

$C_{18}H_{16}N_4O.2HCl.0.30H_2O$; calculated C 56.50%, H 4.90%, N 14.64%, Cl 18.53%; found C 56.71%, H 5.08%, N 14.43%, Cl 18.35%.

3,7-Di(isopropylamidino)dibenzofuran dihydrochloride 7.

$C_{20}H_{24}N_4O.2HCl.0.30H_2O$; calculated C 57.92%, H 6.46%, N 13.51%, Cl 17.10%; found C 58.02%, H 6.49%, N 13.41%, Cl 16.94%.

3,7-Di(N-hydroxylamidino)dibenzofuran dihydrochloride 8.

$C_{14}H_{12}N_4O_3.2HCl.0.3OH_2O$; calculated C 46.37%, H 4.06%, N 15.45%, Cl 19.55%; found C 46.39%, H 4.07%, N 15.38%; Cl 19.55%.

2,8-Dicyanodibenzofuran 11.

$C_{14}H_6N_2O.0.4H_2O$; calculated C 74.60%7 H 3.04%, N 12.43%; found C 74.67%, H 3.06%, N 12.68%.

2-Methoxy-2'-nitro-4,4'-dibromobiphenyl 15.

$C_{13}H_9O_3NBr_2$; calculated C 40.34%, H 2.34%, N 3.62%; found C 40.41%, H 2.33%, N 3.68%.

2-Methoxy-2'-amino-4,4'-dibromobiphenyl 16.

$C_{13}H_{11}ONBr_2$; calculated C 43.73%, H 3.11%, N 3.92%; found C 43.77%, H 3.10%, N 3.89%.

3,7-Dibromo-dibenzofuran 18.

$C_{12}H_6OBr_2$); calculated C 44.21%, H 1.86%, Br 49.02; found C 44.30%, H 1.91%, Br 49.09%.

The foregoing is illustrative of the present invention, and is not to be construed as limiting thereof. The invention is defined by the following claims, with equivalents of the claims to be included therein.

We claim:

1. A compound having the formula:

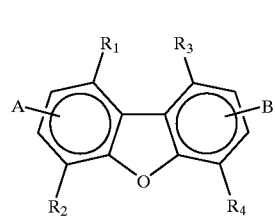

(I)

wherein:
$R_1$, $R_2$, $R_3$, and $R_4$ are each independently selected from the group consisting of H, loweralkyl, oxyalkyl, aryl, alkylaryl, aminoalkyl, aminoaryl, oxyaryl, oxyarylalkyl, or halogen;
A and B are each

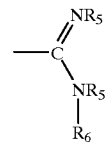

wherein:
each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and
$R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl;
or a pharmaceutically acceptable salt thereof;
subject to the proviso that said compound is not 3:6-diamidinodibenzofuran.

2. A compound according to claim 1, wherein A and B are each:

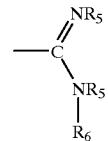

wherein:
$R_1$ is H, $R_2$ is H or loweralkyl, $R_3$ is H, R is H, $R_5$ is H, and $R_6$ is isoalkyl;
and the pharmaceutically acceptable salts thereof.

3. A compound according to claim 1, wherein A and B are each:

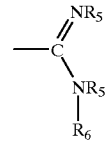

wherein:
$R_1$ is H, $R_2$ is H, $R_3$ is H, R, is H, $R_5$ is H, and $R_6$ is $C_3$–$C_8$ alkoxyalkyl;

and the pharmaceutically acceptable salts thereof.

4. A compound according to claim 1, wherein A and B are each:

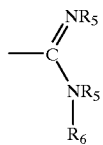

wherein:

$R_1$ is H, $R_2$ is H or loweralkyl, $R_3$ is H, $R_4$ is H, $R_5$ is H, and $R_6$ is alkylhydroxy;

and the pharmaceutically acceptable salts thereof.

5. A compound according to claim 1, wherein A and B are each:

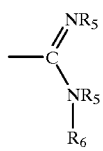

wherein:

$R_1$ is H, $R_2$ is H or loweralkyl, $R_3$ is H, $R_4$ is H, $R_5$ is H, and $R_6$ is propoxyethyl;

and the pharmaceutically acceptable salts thereof.

6. A compound according to claim 1, wherein A and B are each:

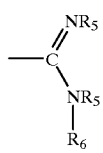

wherein:

$R_1$ is H, $R_2$ is H or loweralkyl, $R_3$ is H, $R_4$ is H, $R_5$ is H, and $R_6$ is propoxyisopropyl;

and the pharmaceutically acceptable salts thereof.

7. A compound according to claim 1, wherein A and B are each:

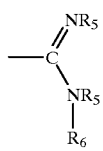

wherein:

$R_1$ is H, $R_2$ is H or loweralkyl, $R_3$ is H, $R_4$ is H, $R_5$ is H, and $R_6$ is aryl or alkylaryl;

and the pharmaceutically acceptable salts thereof.

8. A compound according to claim 1, wherein A and B are each:

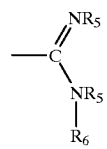

wherein:

$R_1$ is H, $R_2$ is H or loweralkyl, $R_3$ is H, $R_4$ is H, $R_5$ is H, and $R_6$ is alkylcycloalkyl;

and the pharmaceutically acceptable salts thereof.

9. A method of treating *Pneumocystis carinii* pneumonia in a subject in need of such treatment, comprising administering to said subject a compound having the formula:

(I)

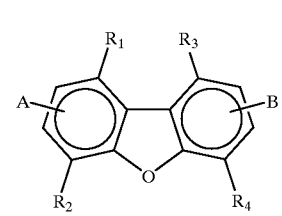

wherein:

$R_1$, $R_2$, $R_3$, and $R_4$ are each independently selected from the group consisting of H, loweralkyl, oxyalkyl, aryl, alkylaryl, aminoalkyl, aminoaryl, oxyaryl, oxyarylalkyl, or halogen;

A and B are each selected from the group consisting of H, loweralkyl, oxyalkyl, and

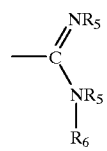

wherein:

each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl;

or a pharmaceutically acceptable salt thereof.

10. A method according to claim 9, wherein A and B are each:

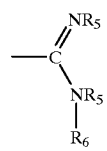

and wherein:

each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl;

or a pharmaceutically acceptable salt thereof.

11. A method according to claim 9, wherein A and B are each:

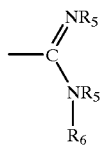

wherein:

$R_1$ is H, $R_2$ is H or loweralkyl, $R_3$ is H, $R_4$ is H, $R_5$ is H, and $R_6$ is isoalkyl;

and the pharmaceutically acceptable salts thereof.

12. A method according to claim 9, wherein A and B are each:

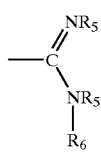

wherein:

$R_1$ is H, $R_2$ is H, $R_3$ is H, $R_4$ is H, $R_5$ is H, and $R_6$ is $C_3$–$C_8$ alkoxyalkyl;

and the pharmaceutically acceptable salts thereof.

13. A method according to claim 9, wherein A and B are each:

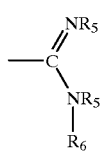

wherein:

$R_1$ is H, $R_2$ is H or loweralkyl, $R_3$ is H, $R_4$ is H, $R_5$ is H, and $R_6$ is alkylhydroxy;

and the pharmaceutically acceptable salts thereof.

14. A method according to claim 9, wherein A and B are each:

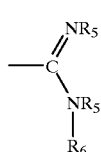

wherein:

$R_1$ is H, $R_2$ is H or loweralkyl, $R_3$ is H, $R_4$ is H, $R_5$ is H, and $R_6$ is propoxyethyl;

and the pharmaceutically acceptable salts thereof.

15. A method according to claim 9, wherein A and B are each:

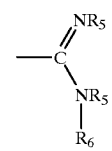

wherein:

$R_1$ is H, $R_2$ is H or loweralkyl, $R_3$ is H, $R_4$ is H, $R_5$ is H, and $R_6$ is propoxyisopropyl;

and the pharmaceutically acceptable salts thereof.

16. A method according to claim 9, wherein A and B are each:

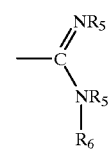

wherein:

$R_1$ is H, $R_2$ is H or loweralkyl, $R_3$ is H, $R_4$ is H, $R_5$ is H, and $R_6$ is aryl or alkylaryl;

and the pharmaceutically acceptable salts thereof.

17. A method according to claim 9, wherein A and B are each:

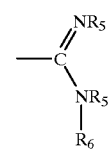

wherein:

$R_1$ is H, $R_2$ is H or loweralkyl, $R_3$ is H, $R_4$ is H, $R_5$ is H, and $R_6$ is alkylcycloalkyl;

and the pharmaceutically acceptable salts thereof.

18. A compound having the formula:

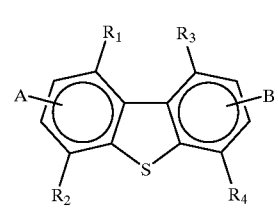

(II)

wherein:

$R_1$, $R_2$, $R_3$, and $R_4$ are each independently selected from the group consisting of H, loweralkyl, oxyalkyl, aryl, alkylaryl, aminoalkyl, aminoaryl, oxyaryl, oxyarylalkyl, or halogen;

A and B are each

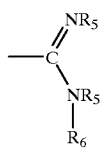

wherein:
  each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and
  $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl;
  or a pharmaceutically acceptable salt thereof.

19. A compound according to claim 18, wherein A and B are each:

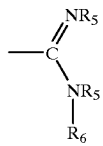

wherein:
  $R_1$ is H, $R_2$ is H or loweralkyl, $R_3$ is H, $R_4$ is H, $R_5$ is H, and $R_6$ is isoalkyl;
  and the pharmaceutically acceptable salts thereof.

20. A compound according to claim 18, wherein A and B are each:

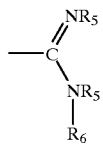

wherein:
  $R_1$ is H, $R_2$ is H, $R_3$ is H, $R_4$ is H, $R_5$ is H, and $R_6$ is $C_3$–$C_8$ alkoxyalkyl;
  and the pharmaceutically acceptable salts thereof.

21. A compound according to claim 18, wherein A and B are each:

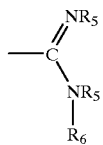

wherein:
  $R_1$ is H, $R_2$ is H or loweralkyl, $R_3$ is H, $R_4$ is H, $R_5$ is H, and $R_6$ is alkylhydroxy;
  and the pharmaceutically acceptable salts thereof.

22. A compound according to claim 18, wherein A and B are each:

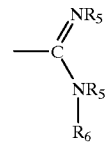

wherein:
  $R_1$ is H, $R_2$ is H or loweralkyl, $R_3$ is H, $R_4$ is H, $R_5$ is H, and $R_6$ is propoxyethyl;
  and the pharmaceutically acceptable salts thereof.

23. A compound according to claim 18, wherein A and B are each:

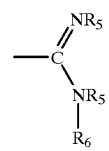

wherein:
  $R_1$ is H, $R_2$ is H or loweralkyl, $R_3$ is H, $R_4$ is H, $R_5$ is H, and $R_6$ is propoxyisopropyl;
  and the pharmaceutically acceptable salts thereof.

24. A compound according to claim 18, wherein A and B are each:

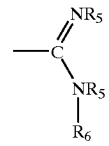

wherein:
  $R_1$ is H, $R_2$ is H or loweralkyl, $R_3$ is H, $R_4$ is H, $R_5$ is H, and $R_6$ is aryl or alkylaryl;
  and the pharmaceutically acceptable salts thereof.

25. A compound according to claim 18, wherein A and B are each:

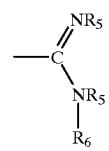

wherein:
  $R_1$ is H, $R_2$ is H or loweralkyl, $R_3$ is H, $R_4$ is H, $R_5$ is H, and $R_6$ is alkylcycloalkyl;
  and the pharmaceutically acceptable salts thereof.

26. A method of treating *Pneumocystis carinii* pneumonia in a subject in need of such treatment, comprising administering to said subject a compound having the formula:

(II)

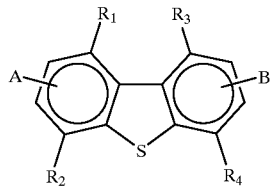

wherein:
$R_1$, $R_2$, $R_3$, and $R_4$ are each independently selected from the group consisting of H, loweralkyl, oxyalkyl, aryl, alkylaryl, aminoalkyl, aminoaryl, oxyaryl, oxyarylalkyl, or halogen;
A and B are each selected from the group consisting of H, loweralkyl, oxyalkyl, and

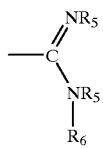

wherein:
each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and
$R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl;
or a pharmaceutically acceptable salt thereof.

27. A method according to claim 26, wherein A and B are each:

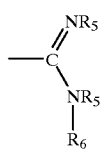

wherein:
$R_1$ is H, $R_2$ is H or loweralkyl, $R_3$ is H, $R_4$ is H, $R_5$ is H, and $R_6$ is isoalkyl;
and the pharmaceutically acceptable salts thereof.

28. A method according to claim 26, wherein A and B are each:

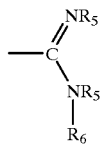

wherein:
$R_1$ is H, $R_2$ is H, $R_3$ is H, $R_4$ is H, $R_5$ is H, and $R_6$ is $C_3$–$C_8$ alkoxyalkyl;
and the pharmaceutically acceptable salts thereof.

29. A method according to claim 26, wherein A and B are each:

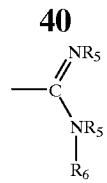

wherein:
$R_1$ is H, $R_2$ is H or loweralkyl, $R_3$ is H, $R_4$ is H, $R_5$ is H, and $R_6$ is alkylhydroxy;
and the pharmaceutically acceptable salts thereof.

30. A method according to claim 26, wherein A and B are each:

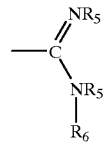

wherein:
$R_1$ is H, $R_2$ is H or loweralkyl, $R_3$ is H, $R_4$ is H, $R_5$ is H, and $R_6$ is propoxyethyl;
and the pharmaceutically acceptable salts thereof.

31. A method according to claim 26, wherein A and B are each:

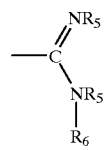

wherein:
$R_1$ is H, $R_2$ is H or loweralkyl, $R_3$ is H, $R_4$ is H, $R_5$ is H, and $R_6$ is propoxyisopropyl;
and the pharmaceutically acceptable salts thereof.

32. A method according to claim 26, wherein A and B are each:

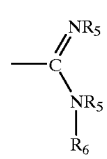

wherein:
$R_1$ is H, $R_2$ is H or loweralkyl, $R_3$ is H, $R_4$ is H, $R_5$ is H, and $R_6$ is aryl or alkylaryl;
and the pharmaceutically acceptable salts thereof.

33. A method according to claim 26, wherein A and B are each:

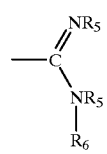

wherein:
$R_1$ is H, $R_2$ is H or loweralkyl, $R_3$ is H, $R_4$ is H, $R_5$ is H, and $R_6$ is alkylcycloalkyl;
and the pharmaceutically acceptable salts thereof.

* * * * *

UNITED STATES PATENT AND TRADEMARK OFFICE
CERTIFICATE OF CORRECTION

PATENT NO. : 6,172,104 B1
DATED : January 9, 2001
INVENTOR(S) : Tidwell et al.

It is certified that error appears in the above-identified patent and that said Letters Patent is hereby corrected as shown below:

Column 1,
Line 9, should read as follows: -- port under Grant Number AI-33363 from the National --

Column 32,
Line 52, should read as follows: -- $R_1$ is H, $R_2$ is H or loweralkyl, $R_3$ is H, $R_4$ is H, $R_5$ is H, --
Line 66, should read as follows: -- $R_1$ is H, $R_2$ is H, $R_3$ is H, $R_4$ is H, $R_5$ is H, and $R_6$ is $C_3$-$C_8$ --

Signed and Sealed this

Twenty-third Day of April, 2002

Attest:

Attesting Officer

JAMES E. ROGAN
Director of the United States Patent and Trademark Office